(12) United States Patent
Gillespie et al.

(10) Patent No.: US 7,345,058 B2
(45) Date of Patent: Mar. 18, 2008

(54) PYRAZOLES

(75) Inventors: Paul Gillespie, Westfield, NJ (US); Robert Alan Goodnow, Jr., Gillette, NJ (US); Qiang Zhang, Parsippany, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 11/395,763

(22) Filed: Mar. 31, 2006

(65) Prior Publication Data

US 2006/0223852 A1 Oct. 5, 2006

Related U.S. Application Data

(60) Provisional application No. 60/668,367, filed on Apr. 5, 2005.

(51) Int. Cl.
- A61K 31/4709 (2006.01)
- A61K 31/4155 (2006.01)
- A61K 31/415 (2006.01)
- C07D 215/08 (2006.01)
- C07D 231/12 (2006.01)

(52) U.S. Cl. .................. 514/314; 514/406; 546/135; 548/374.1

(58) Field of Classification Search .............. 546/164, 546/167, 211, 275.4; 548/364.1, 364.4, 364.7; 514/314, 341, 406

See application file for complete search history.

(56) References Cited

U.S. PATENT DOCUMENTS

| | | | |
|---|---|---|---|
| 4,093,812 A | 6/1978 | Rainer | |
| 4,620,865 A | 11/1986 | Beck et al. | |
| 4,792,565 A | 12/1988 | Shimotori et al. | |
| 5,342,835 A | 8/1994 | Pepin et al. | |
| 5,475,132 A | 12/1995 | Pepin et al. | |
| 2004/0122033 A1 | 6/2004 | Nargund et al. | |
| 2004/0133011 A1 | 7/2004 | Waddell et al. | |
| 2005/0080087 A1 | 4/2005 | Pendri et al. | |

FOREIGN PATENT DOCUMENTS

| | | |
|---|---|---|
| DE | 2612155 | 10/1976 |
| DE | 3713774 | 10/1987 |
| EP | 360701 | 3/1990 |
| JP | 2002003410 | 1/2002 |
| WO | WO 0170671 | 9/2001 |
| WO | WO 0190090 | 11/2001 |
| WO | WO 0190091 | 11/2001 |
| WO | WO 0190092 | 11/2001 |
| WO | WO 0190093 | 11/2001 |
| WO | WO 0190094 | 11/2001 |
| WO | WO 03059267 | 12/2001 |
| WO | WO 0244133 | 6/2002 |
| WO | WO 02076435 A2 | 10/2002 |
| WO | WO 03043999 | 5/2003 |
| WO | WO 03044000 | 5/2003 |
| WO | WO 03044009 | 5/2003 |
| WO | WO 03051845 | 6/2003 |
| WO | WO 03065983 | 8/2003 |
| WO | WO 03075660 | 9/2003 |
| WO | WO 03104207 | 12/2003 |
| WO | WO 03104208 | 12/2003 |
| WO | WO 2004011410 | 2/2004 |
| WO | WO 2004033427 | 4/2004 |
| WO | WO 2004089470 | 4/2004 |
| WO | WO 2004041264 | 5/2004 |
| WO | WO 2004058741 | 7/2004 |
| WO | WO 2004065351 | 8/2004 |
| WO | WO 2004089415 | 10/2004 |
| WO | WO 2004089416 | 10/2004 |
| WO | WO 2004089470 | 10/2004 |
| WO | WO 2004089471 | 10/2004 |
| WO | WO 2004089896 | 10/2004 |
| WO | WO 2004103980 | 12/2004 |
| WO | WO 2004106294 | 12/2004 |
| WO | WO 2004112781 | 12/2004 |

(Continued)

OTHER PUBLICATIONS

R. A. De Fronzo *Drugs* 1999, *58 Suppl. 1*, 29.
S. E. Inzucchi *JAMA* 2002, 287, 360.
R. C. Turner et al. *JAMA* 1999, 281, 2005.
M. Tadayyon and S. A. Smith *Expert Opin. Investig. Drugs* 2003, 12, 307.
M. Salas and J. J. Caro *Adv. Drug React. Tox. Rev.* 2002, 21, 205-217.
E. S. Ford et al. *JAMA* 2002, 287, 356.
Y. Kotolevtsev et al. *Proc. Natl. Acad. Sci. USA* 1997, 94, 14924.
N. M. Morton et al. *J. Biol. Chem.* 2001, 276, 41293.

(Continued)

*Primary Examiner*—Rebecca Anderson
*Assistant Examiner*—Michael P. Barker
(74) *Attorney, Agent, or Firm*—George W. Johnston; Dennis P. Tramaloni; Samuel H. Megerditchian

(57) ABSTRACT

Provided herein are compounds of the formula (I):

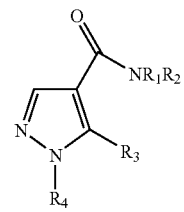

as well as pharmaceutically acceptable salts thereof, wherein the substituents are as those disclosed in the specification. These compounds, and the pharmaceutical compositions containing them, are useful for the treatment of diseases such as, for example, type II diabetes mellitus and metabolic syndrome.

19 Claims, No Drawings

FOREIGN PATENT DOCUMENTS

| WO | WO 2004112782 | 12/2004 |
|---|---|---|
| WO | WO2005016877 | 2/2005 |

OTHER PUBLICATIONS

H. Masuzaki et al. *Science*, 2001, 294, 2166.
B. R. Walker et al. *J. Clin. Endocrinol. Metab.* 1995, 80, 3155.
R. C. Andrews et al. *J. Clin. Enocrinol. Metab.* 2003, 88, 285.
T. C. Sandeep et al. *Proc. Natl. Acad. Sci USA* 2004, 101, 6734.
S. Diederich et al. *Eur. J. Endocrinol.* 2000, 142, 200.
R. A. S. Schweizer et al. *Mol. Cell. Endocrinol.* 2003, 212, 41.
H. H. Wassermann et al. *Tetrahedron Lett.* 1984, 25, 3743-3746.
S. Gelin et al. *Synthesis* 1983, 566-568.
J. Svete et al. *Synthesis* 1990, 70-72.
L. Claisen *Liebigs Ann. Chem.* 1897, 297, 1-18.
L. Crombie et al. *J. Chem. Soc. Perkin Trans. I* 1979, 464-471.
M. S. S. Palanki et al. *J. Med. Chem.* 2000, 43, 3995-4004.
M. T. Herrero et al. *Tetrahedron* 2002, 58, 8581-8589.
J. R. Beck et al. *J. Heterocycl. Chem.* 1987, 24, 739-740.
G. Menozzi et al. *J. Heterocycl. Chem.* 1987, 24, 1669-1676.
H. Ohki et al. *Bioorg. Med. Chem. Lett.* 2002, 12, 3191-3193.
L. De Luca et al. *J. Comb. Chem.* 2003, 5, 465-471.
R. Zupet et al. *J. Heterocycl. Chem.* 1991, 28, 1731-1740.
D. E. Seitz et al. *Tetrahedron Lett.* 1995, 36, 1413-1416.
A. V. Rama Rao et al. *Tetrahedron Lett.* 1990, 31, 1439-42.
P. Kocienski et al. *Tetrahedron Lett.*1988, 29, 4481-4.
J. H. Dewar et al. *J. Chem. Soc.* 1961, 3254-3260.
A. X. Wang et al. *Bioorg. Med. Chem. Lett.* 1998, 8, 2787-2792.
T. A. Elmaati et al. *Pol. J. Chem.* 2002, 76, 945-952.
Chemical Abstracts AN 2002:501464.
G. Giacomelli et al. *Eur. J. Org. Chem.* 2003, 537-541.
F. B. Dains *Chem. Ber.* 1902, 35, 2496-2500.
F. B. Dains et al. *J. Am. Chem. Soc.* 1909, 31, 1148-1157.
F. B. Dains et al. *J. Am. Chem. Soc.* 1918, 40, 562-569.
O. S. Wolfbeis *Chem. Ber.* 1981, 114, 3471-3484.
Chemical Abstracts AN 1987:458919.
F. B. Dains et al. *J. Am. Chem. Soc.* 1916, 38, 1515.
A. N. Borisevich et al. *Ukrainskii Khimicheskii Zhurnal* 1986, 52, 641-7.
M. Kopp et al. *J. Heterocycl. Chem.* 2001, 38, 1045-1050.
J. Svetlik *Heterocycles* 1984, 22, 2513-2516.
J. R. Beck et al. *J. Heterocycl. Chem.* 1987, 24, 267-270.
T. Luebbers et al. *Bioorg. Med. Chem. Lett.* 2000, 10, 821-826.
X.-J. Wang and K. Grozinger *Tetrahedron Lett.* 2000, 41, 4713-4716.
F. Bondavalli et al. *J. Med. Chem.* 2002, 45, 4875-4887.
S. Schenone et al. *Bioorg. Med. Chem. Lett.* 2001, 11, 2529-2531.
P. Seneci et al. *Synth. Commun.* 1999, 29, 311-341.
"Comprehensive Organic Transformations: A Guide to Functional Group Preparations" [R. C. Larock, VCH Publishers, Inc. New York, 1989, pp. 685.
"Comprehensive Organic Transformations: A Guide to Functional Group Preparations" [R. C. Larock, VCH Publishers, Inc. New York, 1989, pp. 694-695.
"Comprehensive Organic Transformations: A Guide. to Functional Group Preparations" [R. C. Larock, VCH Publishers, Inc. New York, 1989, p. 768.
J. March, 3rd Edition, John Wiley & Sons, Inc. New York, 1985], on pp. 437-439.
J. March, 3rd Edition, John Wiley & Sons, Inc. New York, 1985], on pp. 823-824.
H. Emtenäs et al. *J. Org. Chem.* 2001, 26, 6756-6761.
J. Timberlake and J. Stowell; S. Patai Ed.; John Wiley & Sons, Ltd. London 1975, 69-107.
N. I. Ghali et al. *J Org. Chem.* 1981, 46, 5413-5414.
J. Viret et al. *Tetrahedron* 1987, 43, 891-894.
L. F. Audrieth and L. H. Diamond *J. Am. Chem. Soc.* 1954, 76, 4869-4871.
A. Koziara et al. *Synth. Commun.* 1995, 25, 3805-3812.
N. Brosse et al. *Tetrahedron Lett.* 2000, 41, 205-207.
J. Fugger et al. *J. Am. Chem. Soc.* 1955, 77, 1843-1848.
S. Zawadzki et al. *Synthesis* 1987, 485-487.
B. Mlotkowska and Z. Zwierzak *Tetrahedron Lett.* 1978, 19, 4731-4734.
M. S. Gibson; S. Patai Ed.; John Wiley & Sons, Ltd. London 1968, 37-77.
J. March, 3rd Edition, John Wiley & Sons, Inc. New York, 1985, 1153-1154.
R. C. Larock, VCH Publishers, Inc. New York, 1989, 1061-1063.
L. A. Paquette and R. F. Doehner, Jr. *J. Org. Chem.* 1980, 45, 5105-5113.
F. W. Vierhapper and E. L. Eliel *J. Org. Chem.* 1975, 40, 2734-2742.
L. A. Cohen and B. Witkop *J. Am. Chem. Soc.* 1955, 77, 6595-6600.
H. W. Geluk and J. L. M. A. Schlatmann *Tetrahedron* 1968, 24, 5369-5377.
R. C. Larock, VCH Publishers, Inc. New York, 1989[ on pp. 421-423.
R. G. Jones *J. Am. Chem. Soc.* 1952, 74, 4889-4891.
N. J. Cusack et al. *J. Chem. Soc. C* 1971, 1501-1507.

PYRAZOLES

PRIORITY TO RELATED APPLICATIONS

This application claims the benefit of U.S. Provisional Application No. 60/668,367, filed Apr. 5, 2005, which is hereby incorporated by reference in its entirety.

FIELD OF THE INVENTION

The invention relates to inhibitors of 11β-hydroxysteroid dehydrogenase. The inhibitors include, for example, pyrazoles and derivatives thereof and are useful for the treatment of diseases such as type II diabetes mellitus and metabolic syndrome.

All documents cited or relied upon below are expressly incorporated herein by reference.

BACKGROUND OF THE INVENTION

Diabetes mellitus is a serious illness that affects an increasing number of people across the world. Its incidence is increasing along with the increasing trend to obesity in many countries. The serious consequences of the disease include increased risk of stroke, heart disease, kidney damage, blindness, and amputation. Diabetes is characterized by decreased insulin secretion and/or an impaired ability of peripheral tissues to respond to insulin, resulting in increased plasma glucose levels. There are two forms of diabetes: insulin-dependent and non-insulin-dependent, with the great majority of diabetics suffering from the non-insulin-dependent form of the disease, known as type 2 diabetes or non-insulin-dependent diabetes mellitus (NIDDM). Because of the serious consequences, there is an urgent need to control diabetes.

Treatment of NIDDM generally starts with weight loss, a healthy diet and an exercise program. These factors are especially important in addressing the increased cardiovascular risks associated with diabetes, but they are generally ineffective in controlling the disease itself. There are a number of drug treatments available, including insulin, metformin, sulfonylureas, acarbose, and thiazolidinediones. However, each of these treatments has disadvantages, and there is an ongoing need for new drugs to treat diabetes.

Metformin is an effective agent that reduces fasting plasma glucose levels and enhances the insulin sensitivity of peripheral tissue. Metformin has a number of effects in vivo, including an increase in the synthesis of glycogen, the polymeric form in which glucose is stored [R. A. De Fronzo *Drugs* 1999, 58 Suppl. 1, 29]. Metformin also has beneficial effects on lipid profile, with favorable results on cardiovascular health—treatment with metformin leads to reductions in the levels of LDL cholesterol and triglycerides [S. E. Inzucchi *JAMA* 2002, 287, 360]. However, over a period of years, metformin loses its effectiveness [R. C. Turner et al. *JAMA* 1999, 281, 2005] and there is consequently a need for new treatments for diabetes.

Thiazolidinediones are activators of the nuclear receptor peroxisome-proliferator activated receptor-gamma. They are effective in reducing blood glucose levels, and their efficacy has been attributed primarily to decreasing insulin resistance in skeletal muscle [M. Tadayyon and S. A. Smith *Expert Opin. Investig. Drugs* 2003, 12, 307]. One disadvantage associated with the use of thiazolidinediones is weight gain.

Sulfonylureas bind to the sulfonylurea receptor on pancreatic beta cells, stimulate insulin secretion, and consequently reduce blood glucose levels. Weight gain is also associated with the use of sulfonylureas [S. E. Inzucchi *JAMA* 2002, 287, 360] and, like metformin, efficacy decreases over time [R. C. Turner et al. *JAMA* 1999, 281, 2005]. A further problem often encountered in patients treated with sulfonylureas is hypoglycemia [M. Salas and J. J. Caro *Adv. Drug React. Tox. Rev.* 2002, 21, 205-217].

Acarbose is an inhibitor of the enzyme alpha-glucosidase, which breaks down disaccharides and complex carbohydrates in the intestine. It has lower efficacy than metformin or the sulfonylureas, and it causes intestinal discomfort and diarrhea which often lead to the discontinuation of its use [S. E. Inzucchi *JAMA* 2002, 287, 360]

The metabolic syndrome is a condition where patients exhibit more than two of the following symptoms: obesity, hypertriglyceridemia, low levels of HDL-cholesterol, high blood pressure, and elevated fasting glucose levels. This syndrome is often a precursor of type 2 diabetes, and has high prevalence in the United States with an estimated prevalence of 24% (E. S. Ford et al. *JAMA* 2002, 287, 356). A therapeutic agent that ameliorates the metabolic syndrome would be useful in potentially slowing or stopping the progression to type 2 diabetes.

In the liver, glucose is produced by two different processes: gluconeogenesis, where new glucose is generated in a series of enzymatic reactions from pyruvate, and glycolysis, where glucose is generated by the breakdown of the polymer glycogen.

Two of the key enzymes in the process of gluconeogenesis are phosphoenolpyruvate carboxykinase (PEPCK) which catalyzes the conversion of oxalacetate to phosphoenolpyruvate, and glucose-6-phosphatase (G6Pase) which catalyzes the hydrolysis of glucose-6-phosphate to give free glucose. The conversion of oxalacetate to phosphoenolpyruvate, catalyzed by PEPCK, is the rate-limiting step in gluconeogenesis. On fasting, both PEPCK and G6Pase are upregulated, allowing the rate of gluconeogenesis to increase. The levels of these enzymes are controlled in part by the corticosteroid hormones (cortisol in human and corticosterone in mouse). When the corticosteroid binds to the corticosteroid receptor, a signaling cascade is triggered which results in the upregulation of these enzymes.

The corticosteroid hormones are found in the body along with their oxidized 11-dehydro counterparts (cortisone and 11-dehydrocorticosterone in human and mouse, respectively), which do not have activity at the glucocorticoid receptor. The actions of the hormone depend on the local concentration in the tissue where the corticosteroid receptors are expressed. This local concentration can differ from the circulating levels of the hormone in plasma, because of the actions of redox enzymes in the tissues. The enzymes that modify the oxidation state of the hormones are 11beta-hydroxysteroid dehydrogenases forms I and II. Form I (11β-HSD1) is responsible for the reduction of cortisone to cortisol in vivo, while form II (11β-HSD2) is responsible for the oxidation of cortisol to cortisone. The enzymes have low homology and are expressed in different tissues. 11β-HSD1 is highly expressed in a number of tissues including liver, adipose tissue, and brain, while 11β-HSD2 is highly expressed in mineralocorticoid target tissues, such as kidney and colon. 11β-HSD2 prevents the binding of cortisol to the mineralocorticoid receptor, and defects in this enzyme have been found to be associated with the syndrome of apparent mineralocorticoid excess (AME).

Since the binding of the 11β-hydroxysteroids to the corticosteroid receptor leads to upregulation of PEPCK and therefore to increased blood glucose levels, inhibition of 11β-HSD1 is a promising approach for the treatment of diabetes. In addition to the biochemical discussion above, there is evidence from transgenic mice, and also from small clinical studies in humans, that confirm the therapeutic potential of the inhibition of 11β-HSD1.

Experiments with transgenic mice indicate that modulation of the activity of 11β-HSD1 could have beneficial therapeutic effects in diabetes and in the metabolic syndrome. For example, when the 11β-HSD1 gene is knocked out in mice, fasting does not lead to the normal increase in levels of G6Pase and PEPCK, and the animals are not susceptible to stress- or obesity-related hyperglycemia. Moreover, knockout animals which are rendered obese on a high-fat diet have significantly lower fasting glucose levels than weight-matched controls (Y. Kotolevtsev et al. *Proc. Natl. Acad. Sci. USA* 1997, 94, 14924). 11β-HSD1 knockout mice have also been found to have improved lipid profile, insulin sensitivity, and glucose tolerance (N. M. Morton et al. *J. Biol. Chem.* 2001, 276, 41293). The effect of overexpressing the 11β-HSD1 gene in mice has also been studied. These transgenic mice displayed increased 11β-HSD1 activity in adipose tissue and exhibited visceral obesity which is associated with the metabolic syndrome. Levels of the corticosterone were increased in adipose tissue, but not in serum, and the mice had increased levels of obesity, especially when on a high-fat diet. Mice fed on low-fat diets were hyperglycemic and hyperinsulinemic, and also showed glucose intolerance and insulin resistance (H. Masuzaki et al. *Science,* 2001, 294, 2166).

The effects of the non-selective 11β-hydroxysteroid dehydrogenase inhibitor carbenoxolone have been studied in a number of small trials in humans. In one study, carbenoxolone was found to lead to an increase in whole body insulin sensitivity, and this increase was attributed to a decrease in hepatic glucose production (B. R. Walker et al. *J. Clin. Endocrinol. Metab.* 1995, 80, 3155). In another study, decreased glucose production and glycogenolysis in response to glucagon challenge were observed in diabetic but not healthy subjects (R. C. Andrews et al. *J. Clin. Enocrinol. Metab.* 2003, 88, 285). Finally, carbenoxolone was found to improve cognitive function in healthy elderly men and also in type 2 diabetics (T. C. Sandeep et al. *Proc. Natl. Acad. Sci USA* 2004, 101, 6734).

A number of non-specific inhibitors of 11β-HSD1 and 11β-HSD2 have been identified, including glycyrrhetinic acid, abietic acid, and carbenoxolone. In addition, a number of selective inhibitors of 11β-HSD1 have been found, including chenodeoxycholic acid, flavanone and 2'-hydroxyflavanone (S. Diederich et al. *Eur. J. Endocrinol.* 2000, 142, 200 and R. A. S. Schweizer et al. *Mol. Cell. Endocrinol.* 2003, 212, 41).

WO 2004089470, WO 2004089416 and WO 2004089415 (Novo Nordisk A/S); and WO 0190090, WO 0190091, WO 0190092, WO 0190093, WO 03043999, WO 0190094, WO 03044000, WO 03044009, and WO 2004103980 (Biovitrum AB) disclose compounds as inhibitors of 11β-HSD1. These compounds are different in structure from the compounds of the current invention. WO 2004112781 and WO 2004112782 disclose the method of use of some of these compounds for the promotion of wound healing.

WO 03065983, WO 03075660, WO 03104208, WO 03104207, US20040133011, WO 2004058741, WO2005016877 and WO 2004106294 (Merck & Co., Inc.) disclose compounds as inhibitors of 11β-HSD1. These compounds are different in structure from the compounds of the current invention.

US2004122033 discloses the combination of an appetite suppressant with inhibitors of 11β-HSD1 for the treatment of obesity, and obesity-related disorders.

WO 2004065351 (Novartis) discloses compounds as inhibitors of 11β-HSD1. These compounds are different in structure from the compounds of the current invention.

WO 2004089415 (Novo Nordisk A/S) discloses the use of an inhibitor of 11βHSD1 in combination with an agonist of the glucocorticoid receptor for the treatment of diseases including cancer and diseases involving inflammation. Several different classes of 11β-HSD1 inhibitors are disclosed including amino-ketones, benzimidazoles, carboxamides, 2,3-dihydrobenzofuran-7-carboxamides, indoles, methylenedioxyphenylcarboxamides, oxazole-4-carboxamides, oxazole-5-carboxamides pyrazolo[1,5-a]pyrimidines, pyrazole-4-carboxamides, thiazole-4-carboxamides, thiazole-5-carboxamides, and 1,2,4-triazoles.

WO 2004089416 (Novo Nordisk A/S) discloses the use of an inhibitor of 11β-HSD1 in combination with an antihypertensive agent for the treatment of diseases including insulin resistance, dyslipidemia and obesity. WO 2004089470 (Novo Nordisk A/S) discloses substituted amides as inhibitors of 11β-HSD1.

WO 2004089471 (Novo Nordisk A/S) discloses pyrazolo [1,5-a]pyrimidines as inhibitors of 11β-HSD1. WO 2004089896 (Novo Nordisk A/S) discloses compounds as inhibitors of 11β-HSD1. These compounds are different in structure from the compounds of the current invention.

WO 2004011410, WO 2004033427, and WO 2004041264 (AstraZeneca UK Limited) disclose compounds as inhibitors of 11β-HSD1. These compounds are different in structure from the compounds of the current invention.

WO 02076435A2 (The University of Edinburgh) claims the use of an agent which lowers levels of 11β-HSD1 in the manufacture of a composition for the promotion of an atheroprotective lipid profile. Agents mentioned as inhibitors of 11β-HSD 1 include carbenoxolone, 11-oxoprogesterone, 3α,17,21-trihydroxy-5β-pregnan-3-one, 21-hydroxypregn-4-ene-3,11,20-trione, androst-4-ene-3,11,20-trione and 3β-hydroxyandrost-5-en-17-one. None of these compounds is similar in structure to the compounds of the current invention.

WO 03059267 (Rhode Island Hospital) claims a method for treating a glucocorticoid-associated state by the administration of a 11β-HSD1 inhibitor such as 11-ketotestosterone, 11-keto-androsterone, 11-keto-pregnenolone, 11-keto-dehydroepiandrostenedione, 3α,5α-reduced-11-ketoprogesterone, 3α,5α-reduced-11-ketotestosterone, 3α,5α-reduced-11-keto-androstenedione, or 3α,5α-tetrahydro-11β-dehydro-corticosterone. None of these compounds is similar in structure to the compounds of the current invention.

WO 2001070671 (E.I. Du Pont de Nemours & Co.) discloses compounds as insecticides. These compounds are different in structure from the compounds of the current invention.

EP 360701 (Rhone-Poulenc Agrochimie) discloses compounds as agrochemical fungicides. These compounds are different in structure from the compounds of the current invention.

DE 3713774 (Mitsui Toatsu Chemicals, Inc.) discloses compounds as an agrochemical fungicide. These compounds are different in structure from the compounds of the current invention.

A need exits in the art, however, for 11β-HSD1 inhibitors that have efficacy for the treatment of diseases such as type II diabetes mellitus and metabolic syndrome. Further, a need exists in the art for 11β-HSD1 inhibitors having IC50 values less than about 1 μM.

SUMMARY OF THE INVENTION

In one embodiment of the invention, provided is a compound of the formula I:

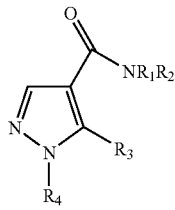

I wherein:
one of $R_1$ or $R_2$ is hydrogen or alkyl and the other is lower alkyl or $(CH_2)_p Y$, wherein Y is a substituted or unsubstituted, saturated, partially unsaturated, or unsaturated mono-, bi- or tri-cyclic 5-10 membered cycloalkyl ring and p is 0 or 1, and wherein substituents on Y are lower alkyl, lower alkoxy, hydroxy, hydroxy-alkyl, alkyl-phenyl, phenyl-alkyl, pyridine or halogen,
or $R_1$ and $R_2$, together with the N atom to which they are attached, form a substituted or unsubstituted ring Z, wherein Z is a 5- to 7-membered monocyclic or 7- to 10-membered bicyclic saturated, partially unsaturated or unsaturated substituted or unsubstituted heterocyclic ring which contains the N atom to which $R_1$ and $R_2$ are attached, and optionally another hetero atom which is selected from N, O and S, wherein the substituted heterocyclic ring is mono- or di-substituted with lower alkyl, hydroxy, hydroxy-alkyl, alkyl-phenyl, phenyl-alkyl, pyridine or halogen;
$R_3$ is an aromatic ring system selected from the group consisting of [2,2']bithiophenyl, 1-methyl-indole, 2,3-dihydro-benzo [1,4]dioxin, benzo[1,3]dioxole, benzo[b] thiophene, benzothiophene, dibenzofuran, furane, naphthalene, phenyl, biphenyl, quinoline, thianthrene and thiophene, wherein said aromatic ring may be unsubstituted or substituted with one or more amino, cyano, formyl, halo, hydroxy, hydroxymethyl, lower-acyl, lower-acyl-amino, lower-alkoxy, lower-alkoxy-carbonyl, 2-(lower-alkoxycarbonyl)-ethenyl, lower-alkyl, lower-alkyl-thio, nitro, trifluoromethoxy or trifluoromethyl, wherein said phenyl ring may additionally be substituted with phenoxy or benzyloxy,
or $R_3$ is:

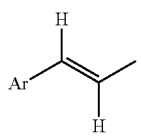

wherein Ar is a carbocyclic or heterocyclic aryl group which may be unsubstituted or substituted with one or more groups selected from the group consisting of halogen, lower alkyl, lower alkoxy, trifluoromethyl, cyano and nitro; and
$R_4$ is lower alkyl;
and pharmaceutically acceptable salts thereof.

In another embodiment of the present invention, a pharmaceutical composition is provided comprising a therapeutically effective amount of a compound according to formula (I) and a pharmaceutically acceptable carrier.

In a further embodiment of the present invention, a method for the treatment of a metabolic disorder in a patient in need thereof is provided, comprising administering to said patient a therapeutically effective amount of a compound according to formula (I).

DETAILED DESCRIPTION OF THE INVENTION

The present invention pertains to inhibitors of 11β-HSD1. In a preferred embodiment, the invention provides for pharmaceutical compositions comprising pyrazoles of the formula I:

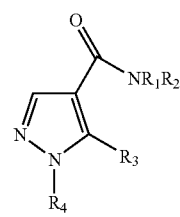

(I)

as well as pharmaceutically acceptable salts thereof, that are useful as inhibitors of 11β-HSD1.

It is to be understood that the terminology employed herein is for the purpose of describing particular embodiments, and is not intended to be limiting. Further, although any methods, devices and materials similar or equivalent to those described herein can be used in the practice or testing of the invention, the preferred methods, devices and materials are now described.

In this specification the term "aryl" is used to mean a mono- or polycyclic aromatic ring system, in which the rings may be carbocyclic or may contain one or more atoms selected from O, S, and N. Examples of aryl groups are phenyl, pyridyl, benzimidazolyl, benzofuranyl, benzothiazolyl, benzothiophenyl, cinnolinyl, furyl, imidazo[4,5-c]pyridinyl, imidazolyl, indolyl, isoquinolinyl, isoxazolyl, naphthyl, [1,7]naphthyridinyl, oxadiazolyl, oxazolyl, phthalazinyl, purinyl, pyidazinyl, pyrazolyl, pyrido[2,3-d]pyrimidinyl, pyrimidinyl, pyrimido[3,2-c]pyrimidinyl, pyrrolo[2,3-d]pyrimidinyl, pyrrolyl, quinazolinyl, quinolinyl, quinoxalinyl, tetrazolyl, thiadiazolyl, thiazolyl, thiophenyl, triazolyl, and the like.

As used herein, the term "alkyl" means, for example, a branched or unbranched, cyclic or acyclic, saturated or unsaturated (e.g. alkenyl or alkynyl) hydrocarbyl radical which may be substituted or unsubstituted. Where cyclic, the alkyl group is preferably $C_3$ to $C_{12}$, more preferably $C_5$ to $C_{10}$, more preferably $C_5$ to $C_7$. Where acyclic, the alkyl group is preferably $C_1$ to $C_{10}$, more preferably $C_1$ to $C_6$, more preferably methyl, ethyl, propyl (n-propyl or isopropyl), butyl (n-butyl, isobutyl or tertiary-butyl) or pentyl (including n-pentyl and isopentyl), more preferably methyl. It will be appreciated therefore that the term "alkyl" as used herein includes alkyl (branched or unbranched), substituted alkyl (branched or unbranched), alkenyl (branched or unbranched), substituted alkenyl (branched or unbranched), alkynyl (branched or unbranched), substituted alkynyl (branched or unbranched), cycloalkyl, substituted cycloalkyl, cycloalkenyl, substituted cycloalkenyl, cycloalkynyl and substituted cycloalkynyl.

As used herein, the term "lower alkyl" means, for example, a branched or unbranched, cyclic or acyclic, saturated or unsaturated (e.g. alkenyl or alkynyl) hydrocarbyl radical wherein said cyclic lower alkyl group is $C_5$, $C_6$ or $C_7$, and wherein said acyclic lower alkyl group is $C_1$, $C_2$, $C_3$ or $C_4$, and is preferably selected from methyl, ethyl, propyl (n-propyl or isopropyl) or butyl (n-butyl, sec-butyl, isobutyl or tertiary-butyl). It will be appreciated therefore that the term "lower alkyl" as used herein includes lower alkyl (branched or unbranched), lower alkenyl (branched or unbranched), lower alkynyl (branched or unbranched), cycloloweralkyl, cycloloweralkenyl and cycloloweralkynyl.

The alkyl and aryl groups may be substituted or unsubstituted. Where substituted, there will generally be, for example, 1 to 3 substituents present, preferably 1 substituent. Substituents may include, for example: carbon-containing groups such as alkyl, aryl, arylalkyl (e.g. substituted and unsubstituted phenyl, substituted and unsubstituted benzyl); halogen atoms and halogen-containing groups such as haloalkyl (e.g. trifluoromethyl); oxygen-containing groups such as alcohols (e.g. hydroxyl, hydroxyalkyl, aryl(hydroxyl)alkyl), ethers (e.g. alkoxy, aryloxy, alkoxyalkyl, aryloxyalkyl), aldehydes (e.g. carboxaldehyde), ketones (e.g. alkylcarbonyl, alkylcarbonylalkyl, arylcarbonyl, arylalkylcarbonyl, arycarbonylalkyl), acids (e.g. carboxy, carboxyalkyl), acid derivatives such as esters (e.g. alkoxycarbonyl, alkoxycarbonylalkyl, alkylcarbonyloxy, alkylcarbonyloxyalkyl), amides (e.g. aminocarbonyl, mono- or di-alkylaminocarbonyl, aminocarbonylalkyl, mono-or di-alkylaminocarbonylalkyl, arylaminocarbonyl), carbamates (e.g. alkoxycarbonylamino, arloxycarbonylamino, aminocarbonyloxy, mono-or di-alkylaminocarbonyloxy, arylaminocarbonyloxy) and ureas (e.g. mono- or di-alkylaminocarbonylamino or arylaminocarbonylamino); nitrogen-containing groups such as amines (e.g. amino, mono- or di-alkylamino, aminoalkyl, mono- or di-alkylaminoalkyl), azides, nitriles (e.g. cyano, cyanoalkyl), nitro; sulfur-containing groups such as thiols, thioethers, sulfoxides and sulfones (e.g. alkylthio, alkylsulfinyl, alkylsulfonyl, alkylthioalkyl, alkylsulfinylalkyl, alkylsulfonylalkyl, arylthio, arysulfinyl, arysulfonyl, arythioalkyl, arylsulfinylalkyl, arylsulfonylalkyl); and heterocyclic groups containing one or more, preferably one, heteroatom, (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and carbolinyl).

The lower alkyl groups may be substituted or unsubstituted, preferably unsubstituted. Where substituted, there will generally be, for example, 1 to 3 substitutents present, preferably 1 substituent.

As used herein, the term "alkoxy" means, for example, alkyl-O— and "alkoyl" means, for example, alkyl-CO—. Alkoxy substituent groups or alkoxy-containing substituent groups may be substituted by, for example, one or more alkyl groups.

As used herein, the term "halogen" means, for example, a fluorine, chlorine, bromine or iodine radical, preferably a fluorine, chlorine or bromine radical, and more preferably a fluorine or chlorine radical.

As used herein, the term "pharmaceutically acceptable salt" means any pharmaceutically acceptable salt of the compound of formula (I). Salts may be prepared from pharmaceutically acceptable non-toxic acids and bases including inorganic and organic acids and bases. Such acids include, for example, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like. Particularly preferred are fumaric, hydrochloric, hydrobromic, phosphoric, succinic, sulfuric and methanesulfonic acids. Acceptable base salts include alkali metal (e.g. sodium, potassium), alkaline earth metal (e.g. calcium, magnesium) and aluminum salts.

General Synthesis of Compounds According to the Invention

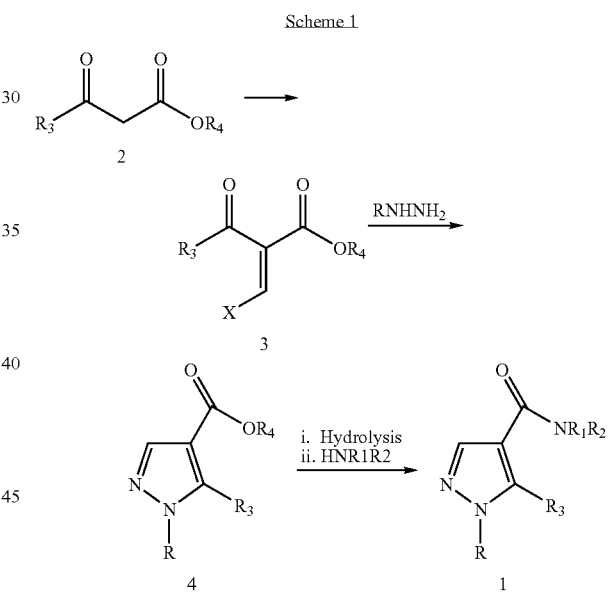

Scheme 1

One general approach to the synthesis of compounds of the invention is shown in Scheme 1. According to this process, a β-keto-ester of formula 2 is converted to a compound of formula 3 where X represents dialkylamino (such as dimethylamino) or lower-alkoxy (such as ethoxy) and then the compound of formula 3 is reacted with a hydrazine to give the compound of formula 4. The ester protective group in the compound of formula 2 is then cleaved and the resulting carboxylic acid is coupled with an amine of formula $HNR_1R_2$ to give the desired compound of formula 1. The reaction of a compound of formula 2 to give a compound of formula 3 can be carried out using conditions that are well known in the art. For example, in the case where X represents dimethylamino, the compound of formula 3 can be prepared by treating a compound of formula 2 with N,N-dimethylformamide dimethyl acetal in an inert solvent such as an aromatic hydrocarbon (for example, toluene) at a temperature between about 50° C. and about 100° C. Examples of conditions for this reaction can be found in the literature, for example, in H. H. Wassermann et al. *Tetrahedron Lett.* 1984, 25, 3743-3746, in S. Gelin et al. *Synthesis* 1983, 566-568, and in J. Svete et al. *Synthesis* 1990, 70-72. In the case where X represents ethoxy, the compound of formula 3 can be prepared by treating a compound of formula 2 with triethylorthoformate in the presence of acetic anhydride at the reflux temperature. Examples of conditions for this reaction can be found in the literature, for example, in L. Claisen *Liebigs Ann. Chem.* 1897, 297, 1-18; in L. Crombie et al. *J. Chem. Soc. Perkin Trans. I* 1979, 464-471; in M. S. S. Palanki et al. *J. Med. Chem.* 2000, 43, 3995-4004; and in M. T. Herrero et al. *Tetrahedron* 2002, 58, 8581-8589.

The reaction of the compound of formula 3 with a hydrazine can be carried out under a variety of conditions. For example, the compound of formula 3 can be reacted with a hydrazine or the acid addition salt of a hydrazine in an inert solvent such as an alcohol (for example, ethanol). In the case where an acid addition salt of the hydrazine is used, then the reaction is carried out in the additional presence of a base such as a tertiary alkylamine (for example, triethylamine or diisopropylethylamine). The reaction is conveniently carried out at a temperature between about −20° C. and about 80° C. Examples of conditions for this reaction can be found in the literature, for example, in J. R. Beck et al. *J. HeterocycL. Chem.* 1987, 24, 739-740; in G. Menozzi et al. *J. Heterocycl. Chem.* 1987, 24, 1669-1676; in F. R. Busch et al. PCT Int. Appl. WO 2003051845; in J. F. Lambert et al. PCT Int. Appl. WO 2002044133; in H. Shimotori et al. U.S. Pat. No. 4,792,565; and in H. Ohki et al. *Bioorg. Med. Chem. Lett.* 2002, 12, 3191-3193.

The cleavage of a compound of formula 4 to the corresponding carboxylic acid is carried out using reaction conditions that are well known in the field of organic synthesis, many of which are outlined in "Protective Groups in Organic Synthesis" [T. W. Greene and P. G. M. Wuts, 2nd Edition, John Wiley & Sons, N.Y. 1991]. For example, in the case where $R_4$ represents methyl or ethyl, the reaction can be conveniently effected by treating the compound with one equivalent of an alkali metal hydroxide, such as potassium hydroxide, sodium hydroxide, or lithium hydroxide, preferably lithium hydroxide, in a suitable solvent, such as a mixture of tetrahydrofuran, methanol, and water. The reaction can be carried out at a temperature between about 0° C. and about room temperature, preferably at about room temperature. As another example, in the case where $R_4$ represents a group that can be cleaved under acidic conditions, such as a tert-butyl group, the ester may be treated with a strong inorganic acid, for example a hydrohalic acid such as hydrogen chloride or hydrogen bromide, or a strong organic acid, for example a halogenated alkane carboxylic acid such as trifluoroacetic acid and the like. The reaction is conveniently carried out in the presence of an inert organic solvent (such as dichloromethane) and at a temperature between about 0° C. and about room temperature, preferably at about room temperature. As a final (but not limiting) example, in the case where R4 represents a group that can be cleaved by catalytic hydrogenation, and with the further condition that the rest of the molecule is stable to such conditions, the reaction may be carried out by hydrogenation in the presence of a noble metal catalyst such as palladium-on-carbon in the presence of an inert solvent (for example, an alcohol such as ethanol) at about room temperature and under atmospheric pressure.

The coupling of a carboxylic acid of structure 4 where $R_4$ represents hydrogen with an amine of structure $HNR_1R_2$, according to Scheme 1, can be achieved using methods well known to one of ordinary skill in the art. For example, the transformation can be carried out by reaction of a carboxylic acid of structure 4 where $R_4$ represents hydrogen or of an appropriate derivative thereof such as an activated ester, with an amine of structure $HNR_1R_2$ or a corresponding acid addition salt (e.g., the hydrochloride salt) in the presence, if necessary, of a coupling agent, many examples of which are well known per se in peptide chemistry. The reaction is conveniently carried out by treating the carboxylic acid of structure 4 where $R_4$ represents hydrogen with the hydrochloride of the amine of structure $HNR_1R_2$ in the presence of an appropriate base, such as diisopropylethylamine, a coupling agent such as O-(benzotriazol-1-yl)-1,1,3,3-tetramethyluronium hexafluorophosphate, and in the optional additional presence of a substance that increases the rate of the reaction, such as 1-hydroxybenzotriazole or 1-hydroxy-7-azabenzotriazole, in an inert solvent, such as a chlorinated hydrocarbon (e.g., dichloromethane) or N,N-dimethylformamide or N-methylpyrrolidinone, at a temperature between about 0° C. and about room temperature, preferably at about room temperature. Alternatively, the reaction can be carried out by converting the carboxylic acid of formula 4 where $R_4$ represents hydrogen to an activated ester derivative, such as the N-hydroxysuccinimide ester, and subsequently reacting this with the amine of structure $HNR_1R_2$ or a corresponding acid addition salt. This reaction sequence can be carried out by reacting the carboxylic acid of formula 4 where $R_4$ represents hydrogen with N-hydroxysuccinimide in the presence of a coupling agent such as N,N'-dicyclohexylcarbodiimide in an inert solvent such as tetrahydrofuran at a temperature between about 0° C. and about room temperature. The resulting N-hydroxysuccinimide ester is then treated with the amine of structure HNR1R2 or a corresponding acid addition salt, in the presence of a base, such as an organic base (e.g., triethylamine or diisopropylethylamine or the like) in a suitable inert solvent such as N,N-dimethylformamide at around room temperature.

The reaction sequence shown in Scheme 1 can also be carried out using solidphase synthesis, in the case where X represents a polymer-bound amino group. Following this approach, the compound of formula 2 is treated with N-formylimidazole dimethyl acetal and a polymer-bound amine such as an aniline-functionalized cellulose derivative (for example, 4-amino-phenyl-sulfonyl-ethoxy-cellulose, which is available from Ionto-sorb, Usti nad Labem, Czech Republic) in the presence of an acid catalyst such as camphor-sulfonic acid in an inert solvent, such as N,N-dimethylformamide at a temperature around 80° C., to give a compound of formula 3 where X represents a polymer-bound aniline. The compound of formula 3 is then converted into the compound of formula 4 by treatment with a hydrazine in an inert solvent such as an alcohol (for example, isopropanol) at a temperature around the boiling point of the solvent. Examples of conditions for this reaction can be found in the literature, for example, in L. De Luca et al. *J. Comb. Chem.* 2003, 5, 465-471.

Scheme 2

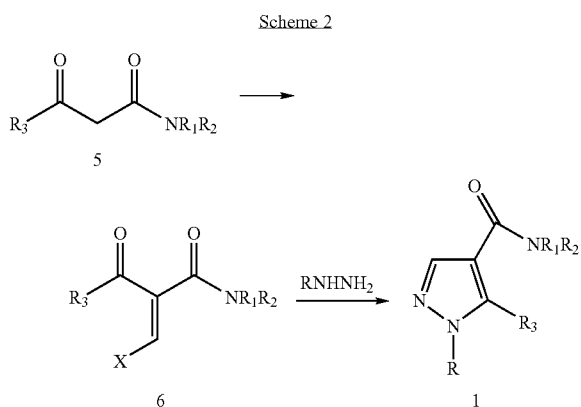

A pyrazole-4-carboxamide of formula 1 can be prepared according to Scheme 2, where a β-keto-amide of formula 5 is converted to a compound of formula 6 where X represents dialkylamino (such as dimethylamino) or lower-alkoxy (such as ethoxy) and then the compound of formula 6 reacts with a hydrazine to give the compound of formula 1. The reaction of a compound of formula 5 to give a compound of formula 6 can be carried out using conditions that are well known in the art. For example, in the case where X represents dimethylamino, the compound of formula 6 can be prepared by treating a compound of formula 5 with N,N-dimethylformamide dimethyl acetal in an inert solvent such as an aromatic hydrocarbon (for example, toluene) at a temperature between about 50° C. and about 100° C. Examples of conditions for this reaction can be found in the literature, for example, in R. Zupet et al. *J. Heterocycl. Chem.* 1991, 28, 1731-1740; in D. E. Seitz et al. *Tetrahedron Lett.* 1995, 36, 1413-1416; in A. V. Rama Rao et al. *Tetrahedron Lett.* 1990, 31, 1439-42; and in P. Kocienski et al. *Tetrahedron Lett.* 1988, 29, 4481-4. In the case where X represents ethoxy, the compound of formula 6 can be prepared by treating a compound of formula 5 with triethylorthoformate in the presence of acetic anhydride at the reflux temperature. Examples of conditions for this reaction can be found in the literature, for example, in J. H. Dewar et al. *J. Chem. Soc.* 1961, 3254-3260.

The reaction of the compound of formula 6 with a hydrazine can be carried out under a variety of conditions. For example, the compound of formula 6 can be reacted with a hydrazine or the acid addition salt of a hydrazine in an inert solvent such as an alcohol (for example, ethanol). In the case where an acid addition salt of the hydrazine is used, then the reaction is carried out in the additional presence of a base such as a tertiary alkylamine (for example, triethylamine or diisopropylethylamine). The reaction is conveniently carried out at a temperature between about −20° C. and about 80° C. Examples of conditions for this reaction can be found in the literature, for example, in A. X. Wang et al. *Bioorg. Med. Chem. Lett.* 1998, 8, 2787-2792; in T. A. Elmaati et al. *Pol. J. Chem.* 2002, 76, 945-952 Chemical Abstracts AN 2002: 501464; and in G. Giacomelli et al. *Eur. J. Org. Chem.* 2003, 537-541

The reaction sequence shown in Scheme 2 can also be carried out in the case where X represents an aniline. Thus, a compound of formula 6 can be prepared from a compound of formula 5 by treatment with an N-(alkoxymethylene)-aniline, in the optional presence of an inert solvent such as kerosene, at elevated temperature such as between about 125° C. and about 140° C. Examples of conditions for this reaction can be found in the literature, for example, in F. B. Dains *Chem. Ber.* 1902, 35, 2496-2500; in F. B. Dains et al. *J. Am. Chem. Soc.* 1909, 31, 1148-1157; in F. B. Dains et al. *J. Am. Chem. Soc.* 1918, 40, 562-569; and in O. S. Wolfbeis *Chem. Ber.* 1981, 114, 3471-3484. The compound of formula 6 can then be converted to the compound of formula 1 by treatment with a hydrazine in an inert solvent such as ethanol at a temperature around the reflux temperature of the solvent. Examples of conditions for this reaction can be found in the literature, for example, in F. B. Dains et al. *J. Am. Chem. Soc.* 1909, 31, 1148-1157; in F. B. Dains et al. *J. Am. Chem. Soc.* 1916, 38, 1515; in F. B. Dains et al. *J. Am. Chem. Soc.* 1918, 40, 562-569; and in A. N. Borisevich et al. *Ukrainskii Khimicheskii Zhurnal* 1986, 52, 641-7 Chemical Abstracts AN 1987:458919.

Scheme 3

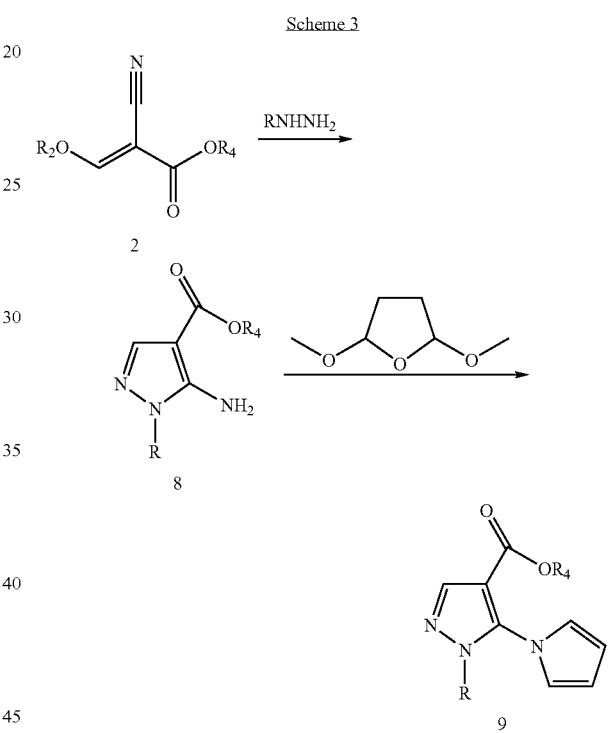

As shown in Scheme 3, a 1-alkyl-5-pyrrolyl-pyrazole-4-carboxylic acid derivative of formula 9 can be prepared starting from a 3-alkoxy-2-cyano-acrylic acid ester of formula 7 by reaction with a hydrazine of formula RNHNH2 to give an intermediate 5-amino-pyrazole of formula 8, which can then be reacted with 2,5-dimethoxy-tetrahydrofuran to give the 5-pyrrolyl-pyrazole of formula 9. This can be converted to a carboxamide of the invention by reactions analogous to those discussed above with reference to Scheme 1. The pyrazole-forming annulation reaction can be conveniently carried out by treating a 3-alkoxy-2-cyano-acrylic acid ester of formula 7 (such as 3-ethoxy-2-cyano-acrylic acid ethyl ester) with a hydrazine of formula RNHNH2 in an inert solvent such as ethanol at the reflux temperature. The subsequent annulation to form the pyrrole ring is conveniently carried out by heating the intermediate 5-amino-pyrazole with 2,5-dimethoxy-tetrahydrofuran in an organic acid such as acetic acid at a temperature of around 100° C. An example of conditions suitable for this process can be found in the literature, for example, in M. Kopp et al.

J. Heterocycl. Chem. 2001, 38, 1045-1050. Further examples of procedures for the preparation of 5-amino-1-aryl-pyrazole-4-carboxylate esters can be found in J. Svetlik Heterocycles 1984, 22, 2513-2516; in J. R. Beck et al. J. Heterocycl. Chem. 1987, 24, 267-270; and in T. Luebbers et al. Bioorg. Med. Chem. Lett. 2000, 10, 821-826. The carboxylate ester of formula 9 can then be hydrolyzed to the corresponding carboxylic acid and coupled with an amine of formula HNR1R2 using procedures analogous to those described above for the conversion of a carboxylate ester of formula 4 to a compound of the invention of formula 1.

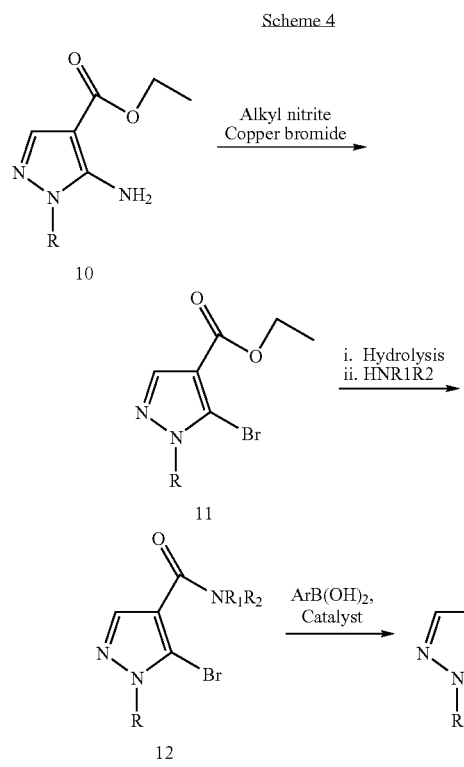

As shown in Scheme 4, a 1-alkyl-5-pyrrolyl-pyrazole-4-carboxylic acid derivative of formula 13 can be prepared starting from a 5-amino-pyrazole-4-carboxylate ester of formula 10 by diazotization of the amino group in the presence of a brominating agent such as copper(II) bromide. The reaction is conveniently carried out by treating the compound of formula 10 with an alkyl nitrite such as tert-butyl nitrite or isoamyl nitrite in an inert solvent such as a halogenated hydrocarbon (for example, carbon tetrachloride) at a temperature around 50° C., in the presence of a bromine source such as bromine, copper(II) bromide, dibromomethane, or bromoform. Conditions appropriate for this reaction can be found in the literature, for example in J. R. Beck and M. P. Lynch U.S. Pat. No. 4,620,865 and in H. Mizukawa JP 2002003410. The conversion of the ester of formula 11 to an amide of formula 12 is analogous to the conversion of a compound of formula 4 to a compound of formula 1 as discussed above, and can be carried out using similar reactions. The conversion of a compound of formula 12 to a compound of the invention of formula 13 can be carried out using a Suzuki reaction with an organoboron intermediate such as an aryl-boronic acid or an ester thereof, a reaction that is well known to one of average skill in the art. For example, the reaction can be conveniently carried out by reacting a compound of formula 12 with an arylboronic acid in a convenient inert solvent such as a polar aprotic solvent (e.g., N,N-dimethylformamide) or an ether (e.g., dioxane) or water, in the presence of a catalytic amount of a palladium(0) complex (e.g., tetrakis(triphenylphosphine)palladium(0)) or a compound which can be reduced in situ to give palladium(0) (for example, palladium(II) acetate or bis(triphenylphosphine)palladium(II) chloride), in the optional additional presence of a catalytic amount of a phosphine ligand, for example tri-o-tolylphosphine or tri-tert-butylphosphine, or alternatively in the presence of a preformed complex of palladium(0) with a phosphine ligand such as bis(tri-cyclohexyl-phosphine)palladium, and also in the presence of an inorganic base, for example, an alkali metal carbonate, bicarbonate, hydroxide or phosphate (e.g., potassium phosphate or sodium carbonate or sodium hydroxide) at a temperature between about room temperature and about 100° C., and preferably at between about room temperature and about 50° C. Conditions appropriate for this reaction can be seen in the literature, for example in X.-J. Wang and K. Grozinger Tetrahedron Lett. 2000, 41, 4713-4716. The starting material of formula 10 can be made from a 3-alkoxy-2-cyano-acrylic acid ester of formula 7 by reaction with an alkyl-hydrazine by reactions analogous to those described above for the preparation of a compound of formula 8. Conditions appropriate for this reaction can be found in the literature, for example in F. Bondavalli et al. J. Med. Chem. 2002, 45, 4875-4887; in S. Schenone et al. Bioorg. Med. Chem. Lett. 2001, 11, 2529-2531; in M. Kopp et al. J. Heterocycl. Chem. 2001, 38, 1045-1050; and in P. Seneci et al. Synth. Commun. 1999, 29, 311-341.

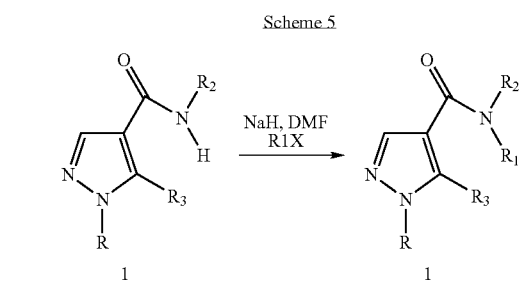

As shown in Scheme 5, a compound of formula 1 in which $R_1$ represents lower alkyl can be prepared from a compound of formula 1 in which $R_1$ represents hydrogen, by reaction with a strong base (such as sodium hydride) in an inert solvent (such as dimethylformamide) at room temperature to give the corresponding anion. This is then reacted without isolation with a lower-alkyl halide of formula R1X, again at room temperature, to give the desired compound of formula 1 in which $R_1$ represents lower alkyl.

Methods suitable for the preparation of many β-keto-esters of formula 2 are known in the literature using a variety of synthetic methods. A listing of many of these methods can be found in "Comprehensive Organic Transformations: A Guide to Functional Group Preparations" [R. C. Larock, VCH Publishers, Inc. New York, 1989], for example on pages 685, 694-695, and 768. Additional examples of synthetic methods appropriate for the preparation of many β-keto-esters of formula 2 can be found in "Advanced Organic Chemistry" [J. March, $3^{rd}$ Edition, John Wiley & Sons, Inc. New York, 1985], on pages 437-439, and 823-824. In addition, more than 100 β-keto-esters of formula 2 are listed as commercially available in the Available Chemicals Directory which is well known to one of average skill in the art of organic synthesis.

Scheme 6

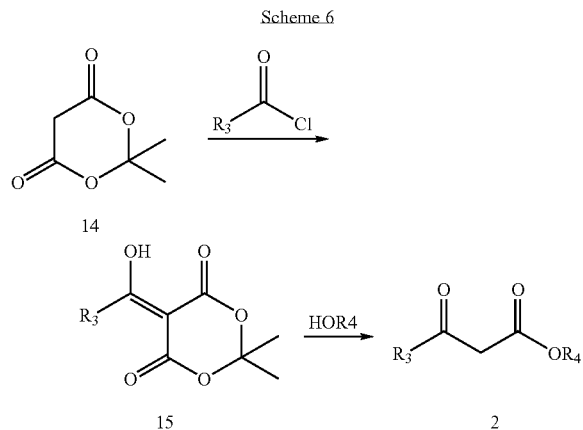

One example of a method to prepare a β-keto-ester of formula 2 is outlined in Scheme 6. Meldrum's acid (14) is treated with an acyl chloride of formula $R_3COCl$ in an anhydrous inert solvent such as a halogenated hydrocarbon (e.g. methylene chloride or ethylene chloride). The reaction is carried out in the presence of an anhydrous organic base, such as pyridine, triethylamine, or diisopropylethylamine, at around room temperature. Conditions suitable for this reaction can be found in the literature, for example in H. Emtenäs et al. J. Org. Chem. 2001, 26, 6756-6761. The resulting intermediate of formula 15 is then heated with an alcohol of formula $HOR_4$, either using the alcohol as solvent (for example in the case where the alcohol is methanol or ethanol), or in an inert solvent such as benzene (for example in the case where the alcohol is benzyl alcohol or tert-butyl alcohol). The reaction is conveniently carried out at a temperature between about 60° C. and about 80° C. Conditions suitable for this reaction can be found in the literature, for example in Y. Oikawa et al. J. Org. Chem. 1978, 43, 2087-2088.

Scheme 7

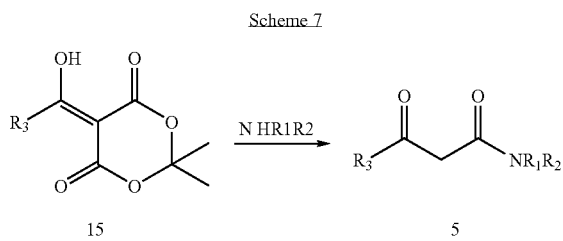

β-Keto-amides of formula 5 can be prepared from the intermediate of formula 15 by treatment with a stoichiometric amount of an amine of formula $HNR_1R_2$ in a suitable inert solvent such as toluene at the refluxing temperature. Conditions suitable for this reaction can be found in the literature, for example in C. S Pak et al. Synthesis 1992, 1213-1214.

A variety of methods are known for the preparation of hydrazines are reviewed in "The Chemistry of the Hydrazo, Azo, and Azoxy Groups. Part 1" [J. Timberlake and J. Stowell; S. Patai Ed.; John Wiley & Sons, Ltd. London 1975, 69-107]. Examples of processes useful for the preparation of alkyl-hydrazines include the reaction of an aldehyde or ketone with a hydrazide followed by reduction and hydrolysis (CH 307629, Chem. Abs. 51:25623; N. I. Ghali et al. J. Org. Chem. 1981, 46, 5413-5414); Hofmann reaction of a urea (J. Viret et al. Tetrahedron 1987, 43, 891-894); electrophilic amination of an alkyl-amine: (L. F. Audrieth and L. H. Diamond J. Am. Chem. Soc. 1954, 76, 4869-4871; A. Koziara et al. Synth. Commun. 1995, 25, 3805-3812); Mitsunobu reaction of an alcohol with N-tert-butoxycarbonylaminophthalimide followed by hydrolysis (N. Brosse et al. Tetrahedron Lett. 2000, 41, 205-207); conversion of an alkyl-amine to the corresponding N-alkyl-sydnone followed by hydrolysis (J. Fugger et al. J. Am. Chem. Soc. 1955, 77, 1843-1848); reaction of an alkyl bromide with N'-isopropylidenephosphorohydrazidic acid diethyl ester or diphenylphosphinic hydrazide followed by deprotection (S. Zawadzki et al. Synthesis 1987, 485-487; B. Mlotkowska and Z. Zwierzak Tetrahedron Lett. 1978, 19, 4731-4734). In addition, more than a dozen substituted or unsubstituted alkyl-hydrazines are listed as commercially available in the Available Chemicals Directory.

Many amines of formula $HNR_1R_2$ are commercially available and known to one skilled in the art. In addition, there are a variety of methods known to one of average skill in the art for the synthesis of amines of formula $HNR_1R_2$. Many of these methods are enumerated in "The Chemistry of the Amino Group" [M. S. Gibson; S. Patai Ed.; John Wiley & Sons, Ltd. London 1968, 37-77], in "Advanced Organic Chemistry" [J. March, 3$^{rd}$ Edition, John Wiley & Sons, Inc. New York, 1985], on pages 1153-1154, and in "Comprehensive Organic Transformations: A Guide to Functional Group Preparations" [R. C. Larock, VCH Publishers, Inc. New York, 1989] on pages 1061-1063. As one example of the preparation of an amine of formula $HNR_1R_2$, a solution of the oxime derived from (1R)-(+)-camphor in an alcohol such as amyl alcohol is treated with sodium added in small pieces over an extended period such as about four hours. The reaction is carried out at the reflux temperature of the solvent, and the product is (−)-endobornylamine hydrochloride, a compound of formula $HR_1R_2$ where $R_1$ represents hydrogen and $R_2$ represents the bornyl moiety. Exact conditions for carrying out this reaction can be found in the literature, for example in L. A. Paquette and R. F. Doehner, Jr. J. Org. Chem. 1980, 45, 5105-5113. As another example of the preparation of an amine of formula $HNR_1R_2$, trans-decahydroquinoline can be prepared by the dissolving metal reduction of $\Delta^{1,9}$-octahydroquinoline which is in turn prepared in a multistep sequence from N-1-cyclohexenylpyrrolidine and acrylonitrile. Conditions for these reactions can be found in F. W. Vierhapper and E. L. Eliel J. Org. Chem. 1975, 40, 2734-2742 and in L. A. Cohen and B. Witkop J. Am. Chem. Soc. 1955, 77, 6595-6600. As a further example of the synthesis of an amine of formula $HNR_1R_2$, 1-hydroxyadamantan-4-one reacts with hydroxylamine hydrochloride in refluxing ethanol in the presence of aqueous sodium hydroxide to give 1-hydroxyadamantan-4-one oxime. This is then reduced with lithium aluminum hydride in an inert solvent such as tetrahydrofuran at the reflux temperature to give 4-aminoadamantan-1-ol, which is conveniently isolated and characterized as the hydrochloride salt. Conditions for these reactions can be found in the literature, for example in H. W. Geluk and J. L. M. A. Schlatmann Tetrahedron 1968, 24, 5369-5377. As a final but not limiting example of the synthesis of an amine of formula $HNR_1R_2$, a secondary amine can be prepared by making use of a-process called reductive amination, which is well known to one of average skill in the art of organic synthesis, whereby an amine is treated with a ketone to give an imine which is reduced by one of a number of reducing agents. Many examples of conditions that can be used for this reaction are enumerated in "Comprehensive Organic Transformations: A Guide to Functional Group Preparations" [R. C. Larock, VCH Publishers, Inc. New York, 1989] on pages 421-423. For example, the amine and ketone can be treated with a reducing agent such as tetrabutylammonium cyanoborohydride in an inert solvent such as a halogenated hydrocarbon (e.g., dichloromethane) in the presence of methanolic HCl at about room temperature.

Starting materials of formula 7 are conveniently prepared by treating a cyanoacetate ester with a trialkyl orthoformate, in the presence of an acid anhydride catalyst such as acetic anhydride, at 80-160° C. Conditions for such a reaction can be found in the literature, for example in R. G. Jones *J. Am. Chem. Soc.* 1952, 74, 4889-4891; in N.J. Cusack et al. *J. Chem. Soc. C* 1971, 1501-1507; and in O. Ackermann et al. U.S. Pat. No. 4,277,418.

In the practice of the method of the present invention, an effective amount of any one of the compounds of this invention or a combination of any of the compounds of this invention or a pharmaceutically acceptable salt thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form or solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

The dose of a compound of the present invention depends on a number of factors, such as, for example, the manner of administration, the age and the body weight of the subject, and the condition of the subject to be treated, and ultimately will be decided by the attending physician or veterinarian. Such an amount of the active compound as determined by the attending physician or veterinarian is referred to herein, and in the claims, as an "effective amount". For example, the dose of a compound of the present invention is typically in the range of about 10 to about 1000 mg per day.

The invention will now be further described in the Examples below, which are intended as an illustration only and do not limit the scope of the invention.

EXAMPLES

Part I: Preferred Intermediates

Reagents were purchased from Aldrich, Sigma, Maybridge, Advanced ChemTech, and Lancaster or other suppliers as indicated below and used without further purification. LC/MS (liquid chromatography/mass spectroscopy) spectra were recorded using the following system. For measurement of mass spectra, the system consists of a Micromass Platform II spectrometer: ES Ionization in positive mode (mass range: 150-1200 amu). The simultaneous chromatographic separation was achieved with the following HPLC system: ES Industries Chromegabond WR C-18 3 u 120 Å (3.2×30 mm) column cartridge; Mobile Phase A: Water (0.02% TFA) and Phase B: Acetonitrile (0.02% TFA); gradient 10% B to 90% B in 3 minutes; equilibration time of 1 minute; flow rate of 2 mL/minute.

Intermediate 1: (5-Bromo-1-methyl-1H-pyrazol-4-yl)-(octahydro-quinolin-1-yl)methanone

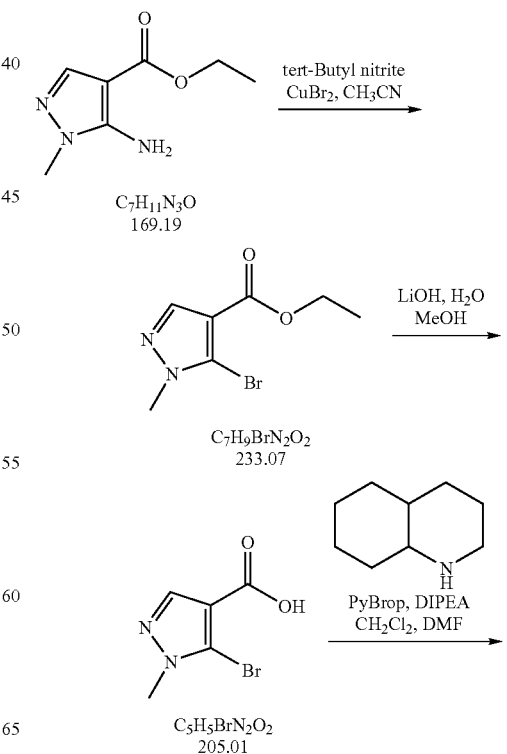

19
-continued

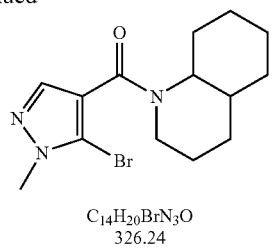

C₁₄H₂₀BrN₃O
326.24

Step 1.
5-Bromo-1-methyl-1H-pyrazole-4-carboxylic acid ethyl ester

To a mixture of t-butyl nitrite (29.5 mL, 221.5 mmol), cupric bromide (39.7 g, 177.5 mmol), and acetonitrile was added 5-amino-1-methyl-1H-pyrazole-4-carboxylic acid ethyl ester (25 g, 148 mmol) in portions over 30 minutes. The reaction mixture was stirred at ambient temperature for 2 h, then at 65° C. for 1 h. The mixture was then poured into 6N HCl (400 mL) and extracted with dichloromethane. After concentration in vacuo, the crude residue was purified by flash chromatography with a gradient of 0-20% ethyl acetate/hexanes to give 5-bromo-1-methyl-1H-pyrazole-4-carboxylic acid ethyl ester (28 g, 81%).

Step 2. (5-Bromo-1-methyl-1H-pyrazol-4-yl)-(octahydro-quinolin-1-yl)-methanone To a solution of 5-bromo-1-methyl-1H-pyrazole-4-carboxylic acid ethyl ester (6.9 g, 29.6 mmol) in CH₃OH (25 mL) and water (25 mL) was added LiOH (0.78 g, 32.6 mmol). The reaction mixture was stirred at reflux for 4 h, and then the solution was concentrated under reduced pressure to remove the methanol. The residue was diluted with water and the solution was acidified to pH 2 with concentrated HCl (~3 mL). The resulting mixture was then extracted with ethyl acetate. The combined organic extracts were concentrated in vacuo to give 5-bromo-1-methyl-1H-pyrazole-4-carboxylic acid, which was used without further purification.

5-Bromo-1-methyl-1H-pyrazole-4-carboxylic acid (29.6 mmol), decahydro-quinoline (Aldrich Chemical Company, Inc., Milwaukee, Wis.; 4.9 g, 35.5 mmol), diisopropylethylamine (11 mL, 59.2 mmol), and PyBrop (bromo-tris-pyrrolidino-phophonium hexafluorophosphate) (Chem-Impex International, Inc., Wood Dale, Ill.; 16.6 g, 35.5 mmol) were mixed together in dry dichloromethane (70 mL) and dry dimethylformamide (20 mL). The mixture was stirred overnight at room temperature. At this time, the mixture was diluted with dichloromethane and extracted three times with water. The combined dichloromethane extracts were evaporated, and the residue was purified by flash chromatography, eluting with 0-10% ethyl acetate/hexanes to give 5-bromo-1-methyl-1H-pyrazol-4-yl)-(octahydro-quinolin-1-yl)-methanone (7.9 g, 82% yield).

20

Intermediate 2:
1-Methyl-5-pyrrol-1-yl-1H-pyrazole-4-carbonyl fluoride

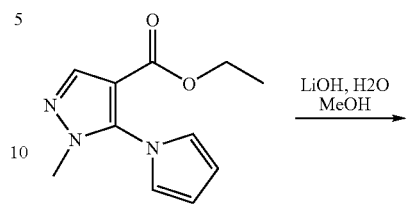

C₁₁H₁₃N₃O₂
219.25

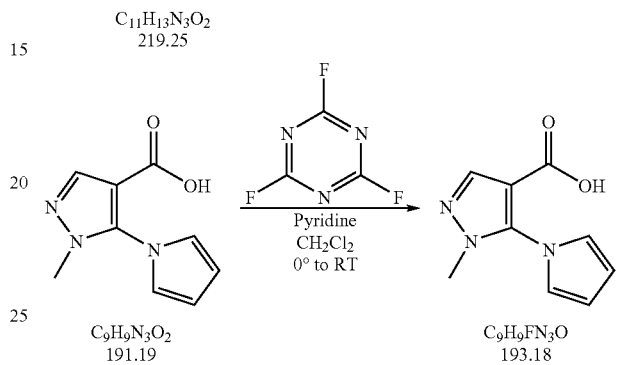

To a solution of 1-methyl-5-pyrrol-1-yl-1H-pyrazole-4-carboxylic acid ethyl ester (Maybridge plc, Cornwall, UK; 20 g, 91.2 mmol) in methanol (100 mL) and water (100 mL) was added LiOH (2.4 g, 100.3 mmol). The reaction mixture was stirred at reflux for 4 hours and then concentrated under reduced pressure to remove the methanol. The residue was diluted with water, acidified to pH 2 with concentrated HCl (9 mL), and extracted with ethyl acetate. The combined extracts were evaporated in vacuo to give 1-methyl-5-pyrrol-1-yl-1H-pyrazole-4-carboxylic acid which was used without further purification.

To a stirred solution of 1-methyl-5-pyrrol-1-yl-1H-pyrazole-4-carboxylic acid (7.65 g, 40 mmol) in dry dichloromethane (150 mL) and pyridine (3.2 mL, 40 mmol) under a nitrogen atmosphere was added cyanuric fluoride (5.4 g, 40 mmol) at 0° C. The reaction mixture was stirred for two hours during which time the reaction temperature was allowed to rise to room temperature. Crushed ice was then added along with additional dichloromethane. The organic layer was separated and the aqueous layer was extracted twice with dichloromethane. Concentration of the combined organic layers under reduced pressure gave 1-methyl-5-pyrrol-1-yl-1H-pyrazole-4-carbonyl fluoride which was used in the next step without further purification.

Intermediate 3: Adamantan-2-yl-isopropyl-amine

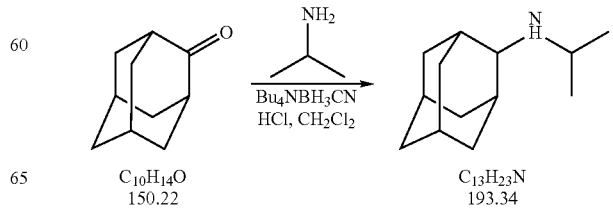

C₁₀H₁₄O
150.22

C₁₃H₂₃N
193.34

Methanolic HCl (2.5 M; 13.3 mmol) is added to a solution of 2-adamantanone (1.00 g, 6.7 mmol) in dichloromethane (25 mL) and then isopropylamine (2.5 mL, 29.4 mmol) is added, followed by tetrabutylammonium cyanoborohydride (1.41 g, 5 mmol) and approximately 1 g of 4A molecular sieves. The reaction mixture is stirred at room temperature until the reaction is complete, as judged by TLC. Then the mixture is filtered and the filtrate is acidified to pH 1 with 1 M HCl, and the solvent is evaporated. The residue is taken up in water and extracted with ether. The aqueous layer is made basic to pH 10 with NaOH solution and the resulting mixture is extracted several times with ether. The combined ether layers are washed with water and brine, dried (magnesium sulfate), filtered, and evaporated to give adamantan-2-yl-isopropyl-amine.

Part II: Preparation of Preferred Compounds

Method A

Preparation of Compounds of the Invention According to Method A

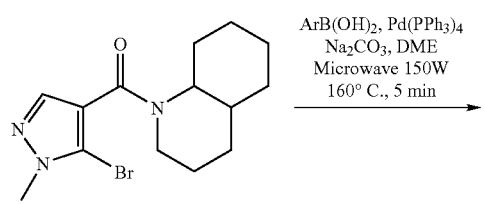

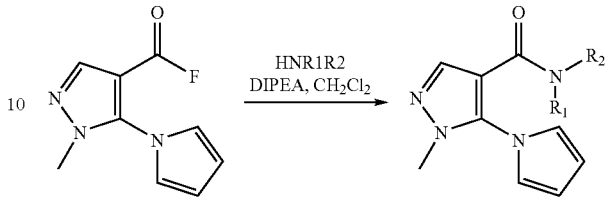

In a Personal Chemistry microwave process tube (Biotage AB, Sweden), tetrakis(triphenylphosphine)palladium (5 mg) was added to a nitrogen degassed mixture of the boronic acid (0.15 mmol), 2M aqueous sodium carbonate solution (2 mL), and (5-bromo-1-methyl-1H-pyrazol-4-yl)-(octahydroquinolin-1-yl)-methanone (of Intermediate 1; 49 mg, 0.15 mmol) in dry DME (1.5 mL). The tube was sealed with a septum and was submitted to 150 W microwave irradiation using a Personal Chemistry Microwave Synthesis system (Biotage AB, Sweden) at 160° C. for 5 minutes. The reaction mixture was cooled to room temperature and then filtered through celite and a silica plug. The eluant was then partitioned between ethyl acetate and water and the water layer was extracted three times with ethyl acetate. The organic layers were combined, concentrated in vacuo and the desired product was obtained after purification by C-18 reversed phase HPLC with a gradient of 10-100% Acetonitrile/Water.

Method B

Preparation of Compounds of the Invention According to Method B

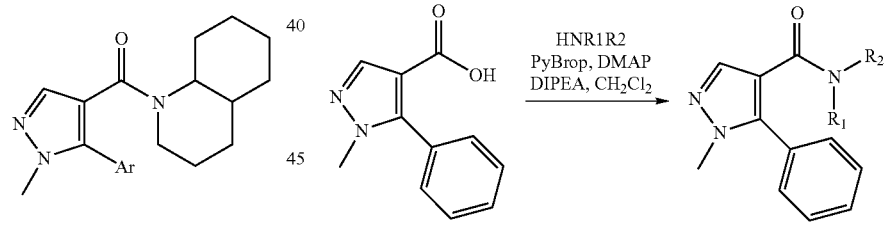

Commercially available amines (0.2 mmol) were distributed to 10 mL screw top Pyrex tubes. To each tube was added 1-methyl-5-pyrrol-1-yl-1H-pyrazole-4-carbonyl fluoride (of Intermediate 2; 39 mg, 0.2 mmol) in dry dichloromethane (2 mL) and diisopropylethylamine (1 mL). The reaction mixture was stirred by agitation at room temperature overnight. At this time, the reaction mixture was diluted with dichloromethane (3 mL) and washed with water (2×2 mL). The organic layers were combined, and concentrated in vacuo. The residue was purified by C-18 reversed phase HPLC with a gradient of 10-100% acetonitrile/water to obtain the desired product.

Method C

Preparation of Compounds of the Invention According to Method C

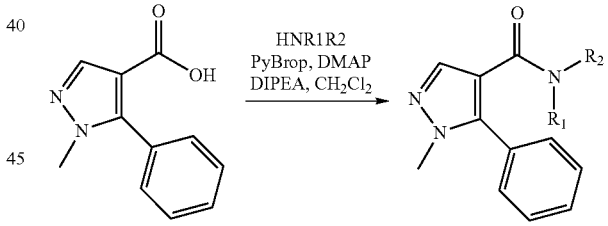

A mixture of the amine (0.2 mmol), 1-methyl-5-phenyl-1H-pyrazole-4-carboxylic acid (40 mg, 0.2 mmol, Maybridge plc, Cornwall, UK), DIPEA (0.14 mL, 0.8 mmol, Aldrich), PyBrop (Chem-Impex International, Inc., Wood Dale, Ill.; 102 mg, 0.8 mmol) and DMAP (0.5 mg, 0.004 mmol, Aldrich) in dry dichloromethane (2 mL) was stirred overnight at room temperature. Water was added and the mixture was extracted three times with dichloromethane. The combined organic extracts were concentrated under reduced pressure purified by C-18 reversed phase HPLC with a gradient of 10-100% acetonitrile/water containing 0.1% TFA as a modifier to give the product.

The compounds of the invention in Examples 1-107 below were prepared by one of the three methods described above.

| Example | Structure | | Name | Synthetic Method | Starting Materials | Measured Mass (M + H) |
|---|---|---|---|---|---|---|
| 1 | (cyclohexyl-piperidine-carbonyl linked to 1-methyl-5-phenyl-1H-pyrazol-4-yl) | | (3-Cyclohexyl-piperidin-1-yl)-(1-methyl-5-phenyl-1H-pyrazol-4-yl)-methanone | C | Methyl-5-phenyl-1H-pyrazole-4-carboxylic acid (Maybridge plc, Cornwall, UK) 3-Cyclohexyl-piperidine hydrochloride (Array Biopharma Inc., Boulder, CO) | 352 |
| 2 | (trans-octahydroisoquinoline linked to 1-methyl-5-phenyl-1H-pyrazol-4-yl) | Relative Stereochemistry | (1-Methyl-5-phenyl-1H-pyrazol-4-yl)-(trans-octahydro-isoquinolin-2-yl)-methanone | C | Methyl-5-phenyl-1H-pyrazole-4-carboxylic acid (Maybridge plc, Cornwall, UK) Trans-Decahydro-isoquinoline (TCI America, Portland, OR) | 324 |
| 3 | (3-benzyl-piperidine linked to 1-methyl-5-phenyl-1H-pyrazol-4-yl) | | (3-Benzyl-piperidin-1-yl)-(1-methyl-5-phenyl-1H-pyrazol-4-yl)-methanone | C | Methyl-5-phenyl-1H-pyrazole-4-carboxylic acid (Maybridge plc, Cornwall, UK) 3-Benzyl-piperidine (Tyger Scientific Inc., Ewing, NJ) | 360 |
| 4 | (3-phenyl-pyrrolidine linked to 1-methyl-5-phenyl-1H-pyrazol-4-yl) | | (1-Methyl-5-phenyl-1H-pyrazol-4-yl)-(3-phenyl-pyrrolidin-1-yl)-methanone | C | Methyl-5-phenyl-1H-pyrazole-4-carboxylic acid (Maybridge plc, Cornwall, UK) 3-Phenyl-pyrrolidine (Array Biopharma Inc., Boulder, CO) | 332 |

-continued

| Example | Structure | Name | Synthetic Method | Starting Materials | Measured Mass (M + H) |
|---|---|---|---|---|---|
| 5 | 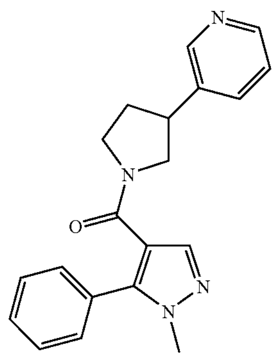 | (1-Methyl-5-phenyl-1H-pyrazol-4-yl)-(3-pyridin-3-yl-pyrrolidin-1-yl)-methanone | C | Methyl-5-phenyl-1H-pyrazole-4-carboxylic acid (Maybridge plc, Cornwall, UK) 3-Pyrrolidin-3-yl-pyridine (Array Biopharma Inc., Boulder, CO) | 333 |
| 6 | 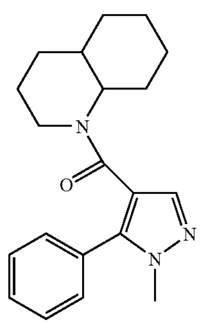 | (1-Methyl-5-phenyl-1H-pyrazol-4-yl)-(octahydro-quinolin-1-yl)-methanone | C | Methyl-5-phenyl-1H-pyrazole-4-carboxylic acid (Maybridge plc, Cornwall, UK) Decahydro-quinoline (Aldrich Chemical Company, Inc., Milwaukee, WI) | 324 |
| 7 | 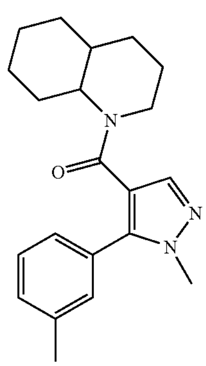 | (1-Methyl-5-m-tolyl-1H-pyrazol-4-yl)-(octahydro-quinolin-1-yl)-methanone | A | Methyl-phenyl-boronic acid quinoline (Aldrich Chemical Company, Inc., Milwaukee, WI) (5-Bromo-1-methyl-1H-pyrazol-4-yl)-(octahydro-quinolin-1-yl)-methanone(Intermediate 1) | 338 |
| 8 | 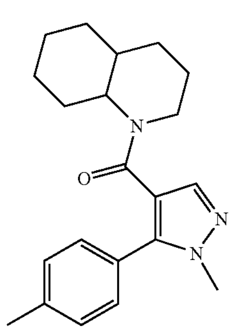 | (1-Methyl-5-p-tolyl-1H-pyrazol-4-yl)-(octahydro-quinolin-1-yl)-methanone | A | Methylphenyl-boronic acid (Combi-Blocks, Inc., San Diego, CA) (5-Bromo-1-methyl-1H-pyrazol-4-yl)-(octahydro-quinolin-1-yl)-methanone (Intermediate 1) | 338 |

-continued

| Example | Structure | Name | Synthetic Method | Starting Materials | Measured Mass (M + H) |
|---------|-----------|------|------------------|--------------------|-----------------------|
| 9 | 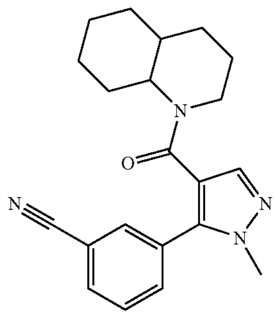 | 3-[2-Methyl-4-(octahydro-quinoline-1-carbonyl)-2H-pyrazol-3-yl]-benzonitrile | A | Cyano-phenyl-boronic acid (Aldrich Chemical Company, Inc., Milwaukee, WI) (5-Bromo-1-methyl-1H-pyrazol-4-yl)-octahydro-quinolin-1-yl)-methanone (Intermediate 1) | 349 |
| 10 | 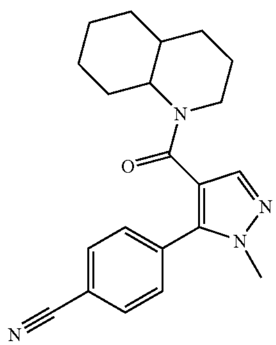 | 4-[2-Methyl-4-(octahydro-quinoline-1-carbonyl)-2H-pyrazol-3-yl]-benzonitrile | A | Cyano-phenyl-boronic acid (Aldrich Chemical Company, Inc., Milwaukee, WI) (5-Bromo-1-methyl-1H-pyrazol-4-yl)-(octahydro-quinolin-1-yl)-methanone (intermediate 1) | 349 |
| 11 | 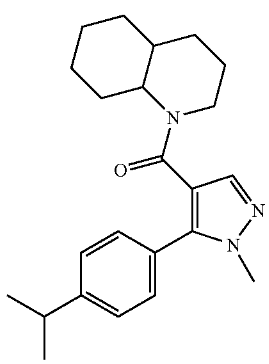 | [5-(4-Isopropyl-phenyl)-1-methyl-1H-pyrazol-4-yl]-(octahydro-quinolin-1-yl)-methanone | A | 4-Isopropyl-phenyl-boronic acid (Lancaster Synthesis Ltd., Lancashire, UK) (5-Bromo-1-methyl-1H-pyrazol-4-yl)-(octahydro-quinolin-1-yl)-methanone(Intermediate 1) | 366 |
| 12 | 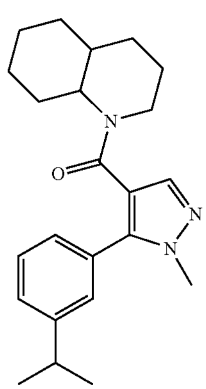 | [5-(3-Isopropyl-phenyl)-1-methyl-1H-pyrazol-4-yl]-(octahydro-quinolin-1-yl)-methanone | A | Isopropyl-phenyl-boronic acid (Lancaster Synthesis Ltd., Lancashire, UK) (5-Bromo-1-methyl-1H-pyrazol-4-yl)-(octahydro-quinolin-1-yl)-methanone(Intermediate 1) | 366 |

-continued

| Example | Structure | Name | Synthetic Method | Starting Materials | Measured Mass (M + H) |
|---------|-----------|------|------------------|--------------------|-----------------------|
| 13 | 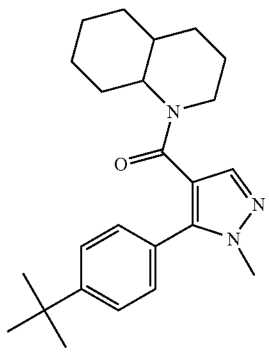 | [5-(4-tert-Butyl-phenyl)-1-methyl-1H-pyrazol-4-yl]-(octahydro-quinolin-1-yl)-methanone | A | tert-Butyl-phenyl-boronic acid (Aldrich Chemical Company, Inc., Milwaukee, WI) (5-Bromo-1-methyl-1H-pyrazol-4-yl)-(octahydro-quinolin-1-yl)-methanone(Intermediate 1) | 380 |
| 14 | 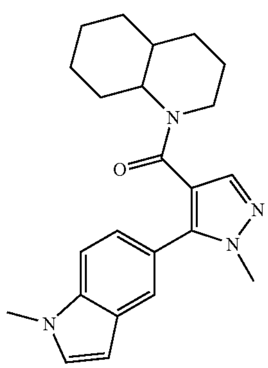 | [1-Methyl-5-(1-methyl-1H-indol-5-yl)-1H-pyrazol-4-yl]-(octahydro-quinolin-1-yl)-methanone | A | 5-(1-Methyl-1H-indole-5-boronic acid (Frontier Scientific, Inc., Logan, UT) (5-Bromo-1-methyl-1H-pyrazol-4-yl)-(octahydro-quinolin-1-yl)-methanone(Intermediate 1) | 377 |
| 15 | 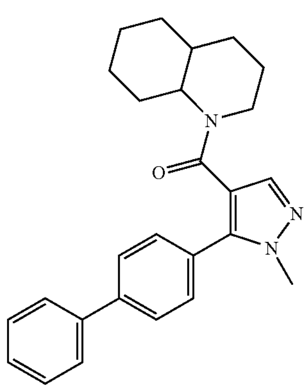 | (5-Biphenyl-4-yl-1-methyl-1H-pyrazol-4-yl)-(octahydro-quinolin-1-yl)-methanone | A | Biphenyl-4-boronic acid (Aldrich Chemical Company, Inc., Milwaukee, WI) (5-Bromo-1-methyl-1H-pyrazol-4-yl)-(octahydro-quinolin-1-yl)-methanone (Intermediate 1) | 400 |

-continued

| Example | Structure | Name | Synthetic Method | Starting Materials | Measured Mass (M + H) |
|---|---|---|---|---|---|
| 16 | 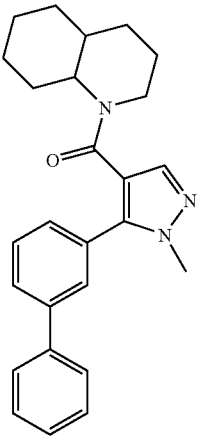 | (5-Biphenyl-3-yl-1-methyl-1H-pyrazol-4-yl)-(octahydro-quinolin-1-yl)-methanone | A | Biphenyl-3-boronic acid (Lancaster Synthesis Ltd., Lancashire, UK) (5-Bromo-1-methyl-1H-pyrazol-4-yl)-(octahydro-quinolin-1-yl)-methanone (Intermediate 1) | 400 |
| 17 | 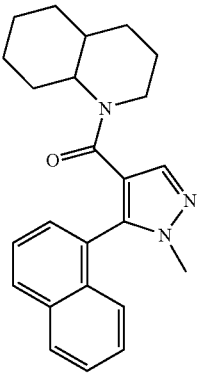 | (1-Methyl-5-naphthalen-1-yl-1H-pyrazol-4-yl)-(octahydro-quinolin-1-yl)-methanone | A | Naphthalene-1-boronic acid (Aldrich Chemical Company, Inc., Milwukee, WI) (5-Bromo-1-methyl-1H-pyrazol-4-yl)-(octahydro-quinolin-1-yl)-methanone (Intermediate 1) | 374 |
| 18 | 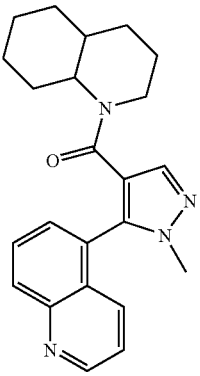 | (1-Methyl-5-quinolin-5-yl-1H-pyrazol-4-yl)-(octahydro-quinolin-1-yl)-methanone | A | Quinoline-5-boronic acid (Matrix Scientific, Columbia, SC) (5-Bromo-1-methyl-1H-pyrazol-4-yl)-(octahydro-quinolin-1-yl)-methanone (Intermediate 1) | 375 |

-continued

| Example | Structure | Name | Synthetic Method | Starting Materials | Measured Mass (M + H) |
| --- | --- | --- | --- | --- | --- |
| 19 | 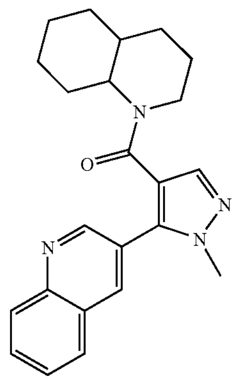 | (1-Methyl-5-quinolin-3-yl-1H-pyrazol-4-yl)-octahydro-quinolin-1-yl)-methanone | A | Quinoline-3-boronic acid (Frontier Scientific, Inc., Logan, UT) (5-Bromo-1-methyl-1H-pyrazol-4-yl)-(octahydro-quinolin-1-yl)-methanone (Intermediate 1) | 375 |
| 20 | 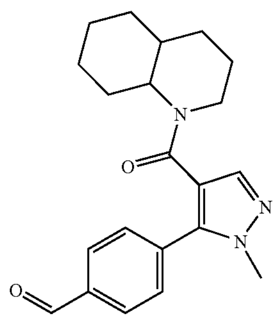 | 4-[2-Methyl-4-(octahydro-quinoline-1-carbonyl)-2H-pyrazol-3-yl]-benzaldehyde | A | Formyl phenylboronic acid (Aldrich Chemical Company, Inc., Milwaukee, WI) (5-Bromo-1-methyl-1H-pyrazol-4-yl)-(octahydro-quinolin-1-yl)-methanone (Intermediate 1) | 352 |
| 21 | 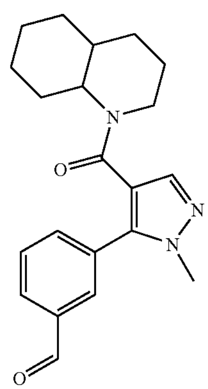 | 3-[2-Methyl-4-(octahydro-quinoline-1-carbonyl)-2H-pyrazol-3-yl]-benzaldehyde | A | Formyl phenylboronic acid (Aldrich Chemical Company, Inc., Milwaukee, WI) (5-Bromo-1-methyl-1H-pyrazol-4-yl)-(octahydro-quinolin-1-yl)-methanone (Intermediate 1) | 352 |
| 22 | 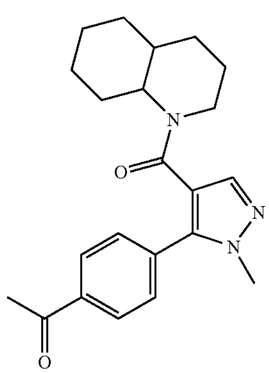 | 1-{4-[2-Methyl-4-(octahydro-quinoline-1-carbonyl)-2H-pyrazol-3-yl]-phenyl}-ethanone | A | Acetyl-phenylboronic acid (Aldrich Chemical Company, Inc., Milwaukee, WI) (5-Bromo-1-methyl-1H-pyrazol-4-yl)-(octahydro-quinolin-1-yl)-methanone(Intermediate 1) | 366 |

-continued

| Example | Structure | Name | Synthetic Method | Starting Materials | Measured Mass (M + H) |
|---------|-----------|------|------------------|--------------------|-----------------------|
| 23 | 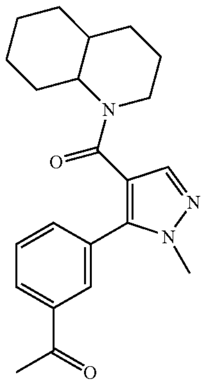 | 1-{3-[2-Methyl-4-(octahydro-quinoline-1-carbonyl)-2H-pyrazol-3-yl]-phenyl}-ethanone | A | Acetyl-phenyl-boronic acid (Aldrich Chemical Company, Inc., Milwaukee, WI) (5-Bromo-1-methyl-1H-pyrazol-4-yl)-(octahydro-quinolin-1-yl)-methanone(Intermediate 1) | 366 |
| 24 | 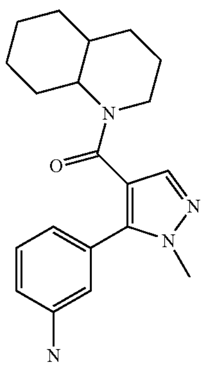 | [5-(3-Amino-phenyl)-1-methyl-1H-pyrazol-4-yl]-(octahydro-quinolin-1-yl)-methanone | A | Amino-phenyl-boronic acid (Alfa Aesar, Ward Hill, MA) (5-Bromo-1-methyl-1H-pyrazol-4-yl)-(octahydro-quinolin-1-yl)-methanone (Intermediate 1) | 339 |
| 25 | 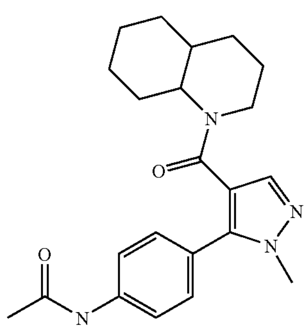 | N-{4-[2-Methyl-4-(octahydro-quinoline-1-carbonyl)-2H-pyrazol-3-yl]-phenyl}-acetamide | A | Acetamido-phenyl-boronic acid (Aldrich Chemical Company, Inc., Milwaukee, WI) (5-Bromo-1-methyl-1H-pyrazol-4-yl)-(octahydro-quinolin-1-yl)-methanone(Intermediate 1) | 381 |
| 26 | 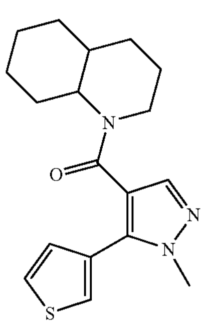 | (1-Methyl-5-thiophen-3-yl-1H-pyrazol-4-yl)-(octahydro-quinolin-1-yl)-methanone | A | Thiophene-3-boronic acid (Aldrich Chemical Company, Inc., Milwaukee, WI) (5-Bromo-1-methyl-1H-pyrazol-4-yl)-(octahydro-quinolin-1-yl)-methanone (Intermediate 1) | 330 |

-continued

| Example | Structure | Name | Synthetic Method | Starting Materials | Measured Mass (M + H) |
|---------|-----------|------|------------------|--------------------|-----------------------|
| 27 | 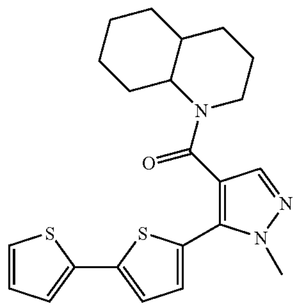 | (5-[2,2']Bithiophenyl-5-yl-1-methyl-1H-pyrazol-4-yl)-(octahydro-quinolin-1-yl)-methanone | A | [2,2']Bithiophenylboronic acid (Maybridge plc, Cornwall, UK) (5-Bromo-1-methyl-1H-pyrazol-4-yl)-(octahydro-quinolin-1-yl)-methanone (Intermediate 1) | 412 |
| 28 | 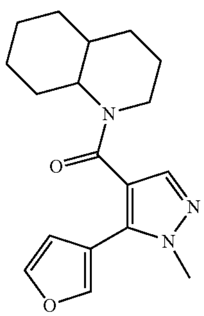 | (5-Furan-3-yl-1-methyl-1H-pyrazol-4-yl)-(octahydro-quinolin-1-yl)-methanone | A | Furan-3-boronic acid (Aldrich Chemical Company, Inc., Milwaukee, WI) (5-Bromo-1-methyl-1H-pyrazol-4-yl)-(octahydro-quinolin-1-yl)-methanone (Intermediate 1) | 314 |
| 29 | 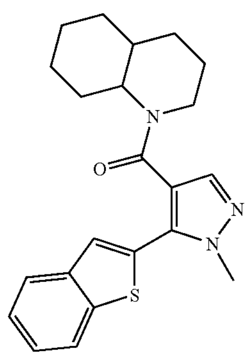 | (5-Benzo[b]thiophen-2-yl-1-methyl-1H-pyrazol-4-yl)-(octahydro-quinolin-1-yl)-methanone | A | Benzothiophen-2-yl-boronic acid (Aldrich Chemical Company, Inc., Milwaukee, WI) (5-Bromo-1-methyl-1H-pyrazol-4-yl)-(octahydro-quinolin-1-yl)-methanone(Intermediate 1) | 380 |
| 30 | 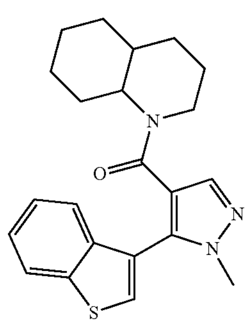 | (5-Benzo[b]thiophen-3-yl-1-methyl-1H-pyrazol-4-yl)-(octahydro-quinolin-1-yl)-methanone | A | Benzothiophen-3-yl-boronic acid (Aldrich Chemical Company, Inc., Milwaukee, WI) (5-Bromo-1-methyl-1H-pyrazol-4-yl)-(octahydro-quinolin-1-yl)-methanone(Intermediate 1) | 380 |

| Example | Structure | Name | Synthetic Method | Starting Materials | Measured Mass (M + H) |
|---|---|---|---|---|---|
| 31 | 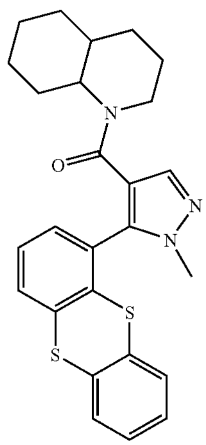 | (1-Methyl-5-thianthren-1-yl-1H-pyrazol-4-yl)-(octahydro-quinolin-1-yl)-methanone | A | Thianthren-1-yl-boronic acid (Aldrich Chemical Company, Inc., Milwaukee, WI) (5-Bromo-1-methyl-1H-pyrazol-4-yl)-(octahydro-quinolin-1-yl)-methanone (Intermediate 1) | 462 |
| 32 | 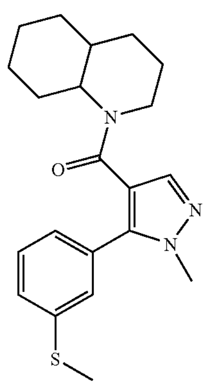 | [1-Methyl-5-(3-methylsulfanyl-phenyl)-1H-pyrazol-4-yl]-(octahydro-quinolin-1-yl)-methanone | A | Methylsulfanyl-phenyl-boronic acid (Combi-Blocks Inc., San Diego, CA) (5-Bromo-1-methyl-1H-pyrazol-4-yl)-(octahydro-quinolin-1-yl)-methanone (Intermediate 1) | 370 |
| 33 | 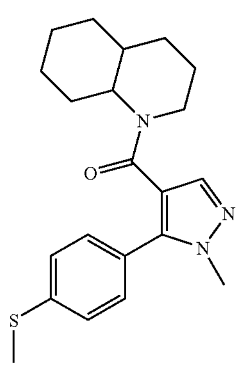 | [1-Methyl-5-(4-methylsulfanyl-phenyl)-1H-pyrazol-2-yl]-(octahydro-quinolin-1-yl)-methanone | A | Methylsulfanyl-phenyl-boronic acid (Aldrich Chemical Company, Inc., Milwaukee, WI) (5-Bromo-1-methyl-1H-pyrazol-4-yl)-(octahydro-quinolin-1-yl)-methanone(Intermediate 1) | 370 |

-continued

| Example | Structure | Name | Synthetic Method | Starting Materials | Measured Mass (M + H) |
|---|---|---|---|---|---|
| 34 | 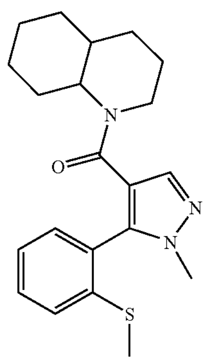 | [1-Methyl-5-(2-methyl-sulfanyl-phenyl)-1H-pyrazol-4-yl]-(octahydro-quinolin-1-yl)-methanone | A | Methylsulfanyl-phenyl-boronic acid (Lancaster Synthesis Ltd., Lancashire, UK) (5-Bromo-1-methyl-1H-pyrazol-4-yl)-(octahydro-quinolin-1-yl)-methanone (Intermediate 1) | 370 |
| 35 | 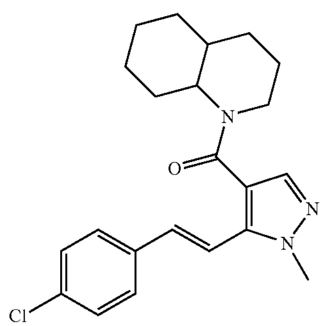 | {5-[(E)-2-(4-Chloro-phenyl)-vinyl]-1-methyl-1H-pyrazol-4-yl}-(octahydro-quinolin-1-yl)-methanone | A | 2-(4-Chloro-phenyl)-vinyl-boronic acid (Aldrich Chemical Company, Inc., Milwaukee, WI) (5-Bromo-1-methyl-1H-pyrazol-4-yl)-(octahydro-quinolin-1-yl)-methanone (Intermediate 1) | 384 |
| 36 | 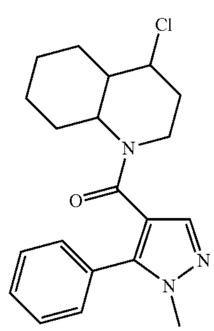 | (4-Chloro-octahydro-quinolin-1-yl)-(1-methyl-5-phenyl)-1H-pyrazol-4-yl)-methanone | C | Methyl-5-phenyl-1H-pyrazole-4-carboxylic acid (Maybridge plc, Cornwall, UK) 4-Chloro-Decahydro-quinoline (Matrix Scientific, Columbia, SC) | 358 |
| 37 | 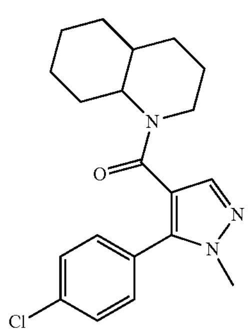 | [5-(4-Chloro-phenyl)-1-methyl-1H-pyrazol-4-yl]-(octahydro-quinolin-1-yl)-methanone | A | Chloro-phenyl-boronic acid (Combi-Blocks Inc., San Diego, CA) (5-Bromo-1-methyl-1H-pyrazol-4-yl)-(octahydro-quinolin-1-yl)-methanone (Intermediate 1) | 358 |

-continued

| Example | Structure | Name | Synthetic Method | Starting Materials | Measured Mass (M + H) |
|---|---|---|---|---|---|
| 38 | 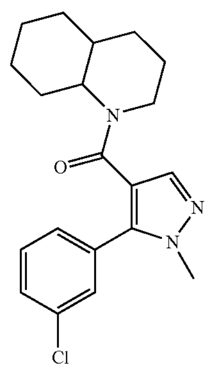 | [5-(3-Chloro-phenyl)-1-methyl-1H-pyrazol-4-yl]-(octahydro-quinolin-1-yl)-methanone | A | Chloro-phenyl-boronic acid (Combi-Blocks Inc., San Diego, CA) (5-Bromo-1-methyl-1H-pyrazol-4-yl)-(octahydro-quinolin-1-yl)-methanone (Intermediate 1) | 358 |
| 39 | 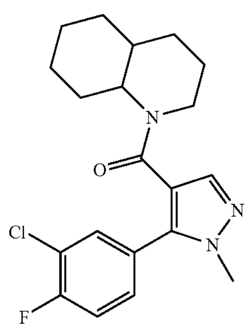 | [5-(3-Chloro-4-fluoro-phenyl)-1-methyl-1H-pyrazol-4-yl]-(octahydro-quinolin-1-yl)-methanone | A | Chloro-4-fluoro-phenyl-boronic acid (Aldrich Chemical Company, Inc., Milwaukee, WI) (5-Bromo-1-methyl-1H-pyrazol-4-yl)-(octahydro-quinolin-1H-yl)-methanone (Intermediate 1) | 376 |
| 40 | 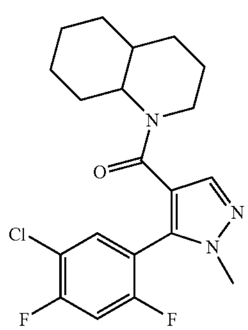 | [5-(5-Chloro-2,4-difluoro-phenyl)-1-methyl-1H-pyrazol-4-yl]-(octahydro-quinolin-1-yl)-methanone | A | Chloro-2,4-difluoro-phenyl-boronic acid (Frontier Scientific, Inc., Logan, UT) (5-Bromo-1-methyl-1H-pyrazol-4-yl)-(octahydro-quinolin-1-yl)-methanone (Intermediate 1) | 394 |
| 41 | 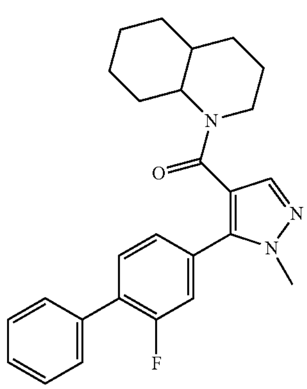 | [5-(2-Fluoro-biphenyl-4-yl-1-methyl-1H-pyrazol-4-yl]-(octahydro-quinolin-1-yl)-methanone | A | Fluoro-biphenyl-4-boronic acid (Aldrich Chemical Company, Inc., Milwaukee, WI) (5-Bromo-1-methyl-1H-pyrazol-4-yl)-(octahydro-quinolin-1-yl)-methanone (Intermediate 1) | 418 |

-continued

| Example | Structure | Name | Synthetic Method | Starting Materials | Measured Mass (M + H) |
|---|---|---|---|---|---|
| 42 | 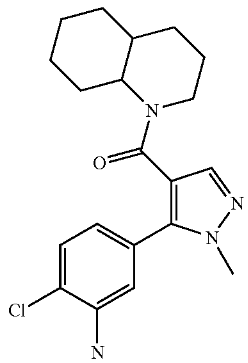 | [5-(3-Amino-4-chloro-phenyl)-1-methyl-1H-pyrazol-4-yl]-(octahydro-quinolin-1-yl)-methanone | A | Amino-4-chloro-phenyl-boronic acid hydrochloride (Combi-Blocks Inc., San Diego, CA) (5-Bromo-1-methyl-1H-pyrazol-4-yl)-(octahydro-quinolin-1-yl)-methanone (Intermediate 1) | 373 |
| 43 | 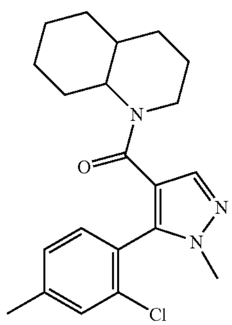 | [5-(2-Chloro-4-methyl-phenyl)-1-methyl-1H-pyrazol-4-yl]-(octahydro-quinolin-1-yl)-methanone | A | Chloro-4-methyl-phenyl-boronic acid (Combi-Blocks Inc., San Diego, CA) (5-Bromo-1-methyl-1H-pyrazol-4-yl)-(octahydro-quinolin-1-yl)-methanone (Intermediate 1) | 372 |
| 44 | 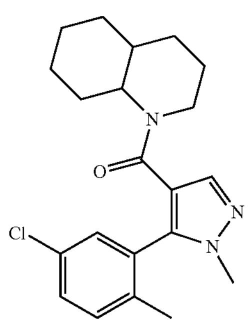 | [5-(5-Chloro-2-methyl-phenyl)-1-methyl-1H-pyrazol-4-yl]-(octahydro-quinolin-1-yl)-methanone | A | Chloro-2-methyl-phenyl-boronic acid (Matrix Scientific, Columbia, SC) (5-Bromo-1-methyl-1H-pyrazol-4-yl)-(octahydro-quinolin-1-yl)-methanone (Intermediate 1) | 372 |
| 45 | 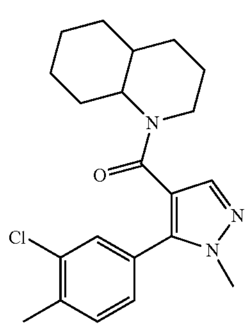 | [5-(3-Chloro-4-methyl-phenyl)-1-methyl-1H-pyrazol-4-yl]-(octahydro-quinolin-1-yl)-methanone | A | Chloro-4-methyl-phenyl-boronic acid (Combi-Blocks Inc., San Diego, CA) (5-Bromo-1-methyl-1H-pyrazol-4-yl)-(octahydro-quinolin-1-yl)-methanone (Intermediate 1) | 372 |

-continued

| Example | Structure | Name | Synthetic Method | Starting Materials | Measured Mass (M + H) |
|---|---|---|---|---|---|
| 46 | 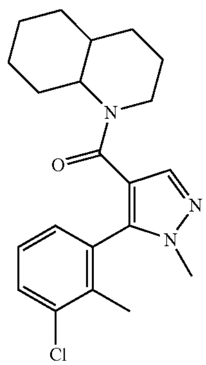 | [5-(3-Chloro-2-methyl-phenyl)-1-methyl-1H-pyrazol-4-yl]-(octahydro-quinolin-1-yl)-methanone | A | Chloro-2-methyl-phenyl-boronic acid (Combi-Blocks Inc., San Diego, CA) (5-Bromo-1-methyl-1H-pyrazol-4-yl)-octahydro-quinolin-1-yl)-methanone (Intermediate 1) | 372 |
| 47 | 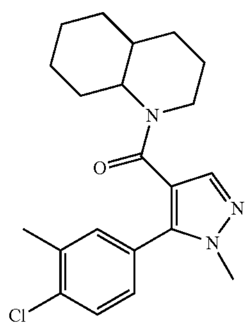 | [5-(4-Chloro-3-methyl-phenyl)-1-methyl-1H-pyrazol-4-yl]-(octahydro-quinolin-1-yl)-methanone | A | Chloro-3-methyl-phenyl-boronic acid (Combi-Blocks Inc., San Diego, CA) (5-Bromo-1-methyl-1H-pyrazol-4-yl)-(octahydro-quinolin-1-yl)-methanone (Intermediate 1) | 372 |
| 48 | 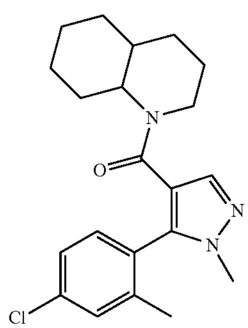 | [5-(4-Chloro-2-methyl-phenyl)-1-methyl-1H-pyrazol-4-yl]-(octahydro-quinolin-1-yl)-methanone | A | Chloro-2-methyl-phenyl-boronic acid (Combi-Blocks Inc., San Diego, CA) (5-Bromo-1-methyl-1H-pyrazol-4-yl)-octahydro-quinolin-1-yl)-methanone (Intermediate 1) | 372 |
| 49 | 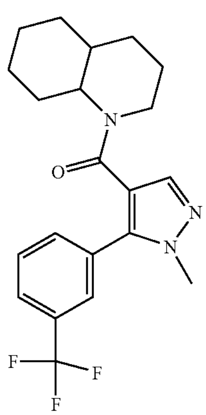 | [1-Methyl-5-(3-trifluoromethyl-phenyl)-1H-pyrazol-4-yl]-(octahydro-quinolin-1-yl)-methanone | A | 3-Trifluoromethyl-phenyl-boronic acid (Combi-Blocks Inc., San Diego, CA) (5-Bromo-1-methyl-1H-pyrazol-4-yl)-(octahydro-quinolin-1-yl)-methanone (Intermediate 1) | 392 |

| Example | Structure | Name | Synthetic Method | Starting Materials | Measured Mass (M + H) |
|---------|-----------|------|------------------|--------------------|-----------------------|
| 50 | 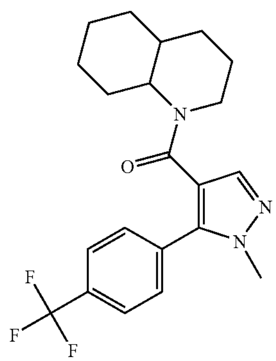 | [1-Methyl-5-(4-trifluoromethyl-phenyl)-1H-pyrazol-4-yl]-(octahydro-quinolin-1-yl)-methanone | A | Trifluoromethyl-phenyl-boronic acid (Aldrich Chemical Company, Inc., Milwaukee, WI) (5-Bromo-1-methyl-1H-pyrazol-4-yl)-(octahydro-quinolin-1-yl)-methanone (Intermediate 1) | 392 |
| 51 | 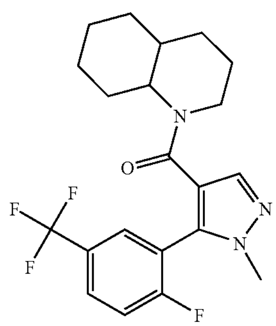 | [5-(2-Fluoro-5-trifluoromethyl-phenyl)-1-methyl-1H-pyrazol-4-yl]-(octahydro-quinolin-1-yl)-methanone | A | 2-Fluoro-5-trifluoromethyl-phenyl-boronic acid (Aldrich Chemical Company, Inc., Milwaukee, WI) (5-Bromo-1-methyl-1H-pyrazol-4-yl)-(octahydro-quinolin-1-yl)-methanone (Intermediate 1) | 410 |
| 52 | 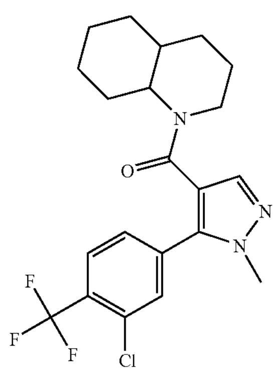 | [5-(3-Chloro-4-trifluoromethyl-phenyl)-1-methyl-1H-pyrazol-4-yl]-(octahydro-quinolin-1-yl)-methanone | A | 3-Chloro-4-trifluoromethyl-phenyl-boronic acid (Combi-Blocks Inc., San Diego, CA) (5-Bromo-1-methyl-1H-pyrazol-4-yl)-(octahydro-quinolin-1-yl)-methanone (Intermediate 1) | 426 |
| 53 | 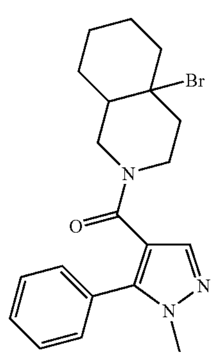 | (4a-Bromo-octahydro-isoquinolin-2-yl)-(1-methyl-5-phenyl-1H-pyrazol-4-yl)-methanone | C | Methyl-5-phenyl-1H-pyrazole-4-carboxylic acid (Maybridge plc, Cornwall, UK) 4a-Bromo-perhydroisoquinoline hydrobromide (Maybridge plc, Cornwall, UK) | 402 |

-continued

| Example | Name | Synthetic Method | Starting Materials | Measured Mass (M + H) |
|---|---|---|---|---|
| 54 | [1-Methyl-5-(3-nitro-phenyl)-1H-pyrazol-4-yl]-(octahydro-quinolin-1-yl)-methanone | A | Nitrophenyl-boronic acid (Aldrich Chemical Company, Inc., Milwaukee, WI) (5-Bromo-1-methyl-1H-pyrazol-4-yl)-(octahydro-quinolin-1-yl)-methanone (Intermediate 1) | 369 |
| 55 | [1-Methyl-5-(4-nitro-phenyl)-1H-pyrazol-4-yl]-(octahydro-quinolin-1-yl)-methanone | A | Nitrophenyl-boronic acid (Combi-Blocks Inc., San Diego, CA) (5-Bromo-1-methyl-1H-pyrazol-4-yl)-(octahydro-quinolin-1-yl)-methanone (Intermediate 1) | 369 |
| 56 | 3-[2-Methyl-4-(octahydro-quinoline-1-carbonyl)-2H-pyrazol-3-yl]-benzoic acid methyl ester | A | Phenyl-boronic acid methyl ester (Combi-Blocks, Inc., San Diego, CA) (5-Bromo-1-methyl-1H-pyrazol-4-yl)-(octahydro-quinolin-1-yl)-methanone (Intermediate 1) | 382 |

-continued

| Example | Structure | Name | Synthetic Method | Starting Materials | Measured Mass (M + H) |
|---|---|---|---|---|---|
| 57 | 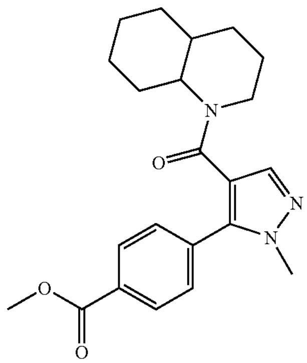 | 4-[2-Methyl-4-(octa-hydro-quinoline-1-carbonyl)-2H-pyrazol-3-yl]-benzoic acid methyl ester | A | Benzoic acid methyl ester boronic ester (Combi-Blocks Inc., San Diego, CA) (5-Bromo-1-methyl-1H-pyrazol-4-yl)-(octa-hydro-quinolin-1-yl)-methanone (Intermediate 1) | 382 |
| 58 | 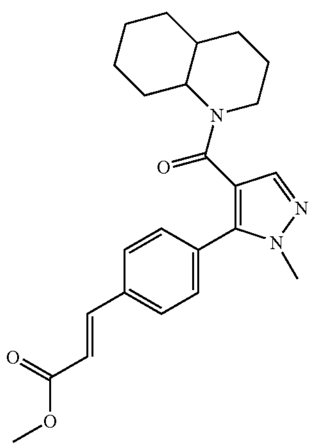 | (E)-3-{4-[2-Methyl-4-(octa-hydro-quinoline-1-carbonyl)-2H-pyrazol-3-yl]-phenyl}-acrylic acid methyl ester | A | 4-(2-Methoxy-carbonyl-vinyl)-phenyl-boronic acid (Combi-Blocks Inc., San Diego, CA) (5-Bromo-1-methyl-1H-pyrazol-4-yl)-(octa-hydro-quinolin-1-yl)-methanone (Intermediate 1) | 408 |
| 59 | 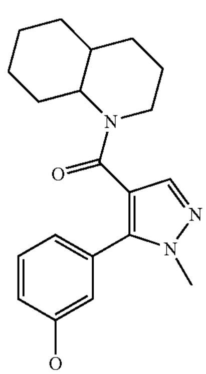 | [5-(3-Hydroxy-phenyl)-1-methyl-1H-pyrazol-4-yl]-(octa-hydro-quinolin-1-yl)-methanone | A | 3-Hydroxyphenyl-boronic acid (Aldrich Chemical Company, Inc., Milwaukee, WI) (5-Bromo-1-methyl-1H-pyrazol-4-yl)-(octa-hydro-quinolin-1-yl)-methanone (Intermediate 1) | 340 |

-continued

| Example | Structure | Name | Synthetic Method | Starting Materials | Measured Mass (M + H) |
|---|---|---|---|---|---|
| 60 | 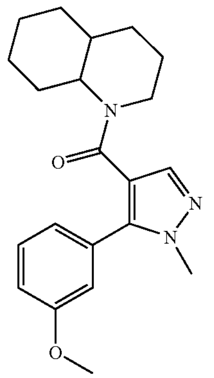 | [5-(3-Methoxy-phenyl)-1-methyl-1H-pyrazol-4-yl]-(octahydro-quinolin-1-yl)-methanone | A | 3-Methoxyphenyl-boronic acid (Aldrich Chemical Company, Inc., Milwaukee, WI) (5-Bromo-1-methyl-1H-pyrazol-4-yl)-(octahydro-quinolin-1-yl)-methanone (Intermediate 1) | 354 |
| 61 | 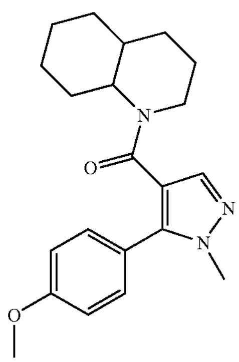 | [5-(4-Methoxy-phenyl)-1-methyl-1H-pyrazol-4-yl]-(octahydro-quinolin-1-yl)-methanone | A | 4-Methoxyphenyl-boronic acid (Aldrich Chemical Company, Inc., Milwaukee, WI) (5-Bromo-1-methyl-1H-pyrazol-4-yl)-(octahydro-quinolin-1-yl)-methanone (Intermediate 1) | 354 |
| 62 | 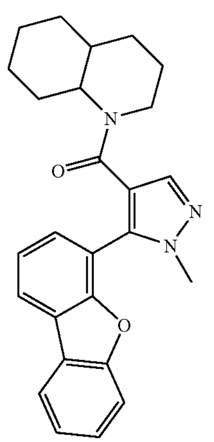 | (5-Dibenzofuran-4-yl-1-methyl-1H-pyrazol-4-yl)-(octahydro-quinolin-1-yl)-methanone | A | Dibenzofuran-4-boronic acid (Aldrich Chemical Company, Inc., Milwaukee, WI) (5-Bromo-1-methyl-1H-pyrazol-4-yl)-(octahydro-quinolin-1-yl)-methanone (Intermediate 1) | 414 |

-continued

| Example | Structure | Name | Synthetic Method | Starting Materials | Measured Mass (M + H) |
|---|---|---|---|---|---|
| 63 | 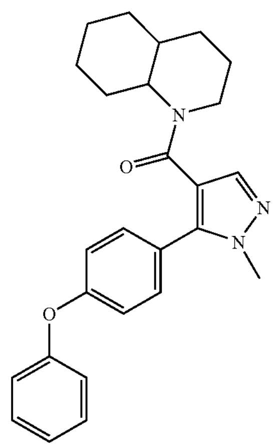 | [1-Methyl-5-(4-phenoxy-phenyl)-1H-pyrazol-4-yl]-(octahydro-quinolin-1-yl)-methanone | A | 4-Phenoxy-phenyl-boronic acid (Aldrich Chemical Company, Inc., Milwaukee, WI) (5-Bromo-1-methyl-1H-pyrazol-4-yl)-(octahydro-quinolin-1-yl)-methanone (Intermediate 1) | 416 |
| 64 | 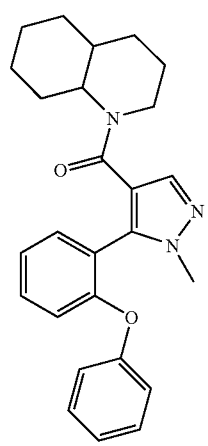 | [1-Methyl-5-(2-phenoxy-phenyl)-1H-pyrazol-4-yl]-(octahydro-quinolin-1-yl)-methanone | A | 2-Phenoxy-phenyl-boronic acid (Aldrich Chemical Company, Inc., Milwaukee, WI) (5-Bromo-1-methyl-1H-pyrazol-4-yl)-(octahydro-quinolin-1-yl)-methanone (Intermediate 1) | 416 |
| 65 | 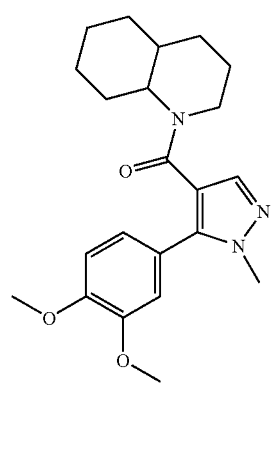 | [5-(3,4-Dimethoxy-phenyl)-1-methyl-1H-pyrazol-4-yl]-(octahydro-quinolin-1-yl)-methanone | A | 3,4-Dimethoxy-phenyl-boronic acid (Aldrich Chemical Company, Inc., Milwaukee, WI) (5-Bromo-1-methyl-1H-pyrazol-4-yl)-(octahydro-quinolin-1-yl)-methanone (Intermediate 1) | 384 |

| Example | Structure | Name | Synthetic Method | Starting Materials | Measured Mass (M + H) |
|---------|-----------|------|------------------|---------------------|------------------------|
| 66 | 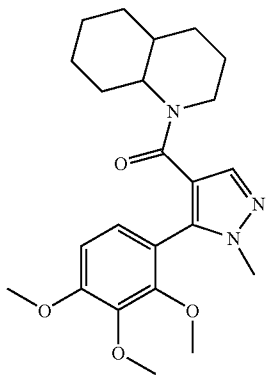 | [1-Methyl-5-(2,3,4-tri-methoxy-phenyl)-1H-py-razol-4-yl]-(octa-hydro-quinolin-1-yl)-meth-anone | A | 2,3,4-Trimeth-oxy-phenyl-boronic acid (Aldrich Chemical Company, Inc., Milwaukee, WI) (5-Bromo-1-methyl-1H-pyrazol-4-yl)-(octa-hydro-quinolin-1-yl)-methanone (Intermediate 1) | 414 |
| 67 | 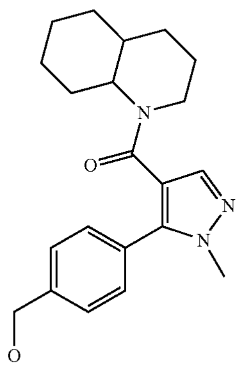 | [5-(4-Hydroxy-methyl-phenyl)-1-methyl-1H-pyrazol-4-yl]-(octa-hydro-quinolin-1-yl)-meth-anone | A | 4-Hydroxymethyl-phenyl-boronic acid (Aldrich Chemical Company, Inc., Milwaukee, WI) (5-Bromo-1-methyl-1H-pyrazol-4-yl)-(octa-hydro-quinolin-1-yl)-methanone (Intermediate 1) | 354 |
| 68 | 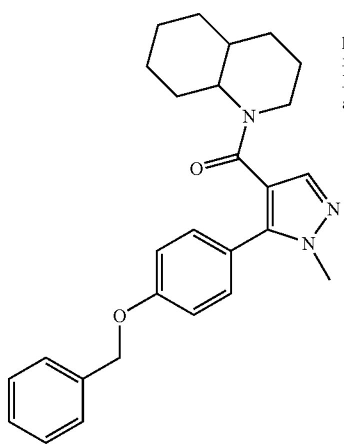 | [5-(4-Benzyloxy-phenyl)-1-methyl-1H-pyrazol-4-yl]-(octa-hydro-quinolin-1-yl)-meth-anone | A | 4-Benzyloxyphenyl-boronic acid (Combi-Blocks Inc., San Diego, CA) (5-Bromo-1-methyl-1H-pyrazol-4-yl)-(octa-hydro-quinolin-1-yl)-methanone (Intermediate 1) | 430 |
| 69 | 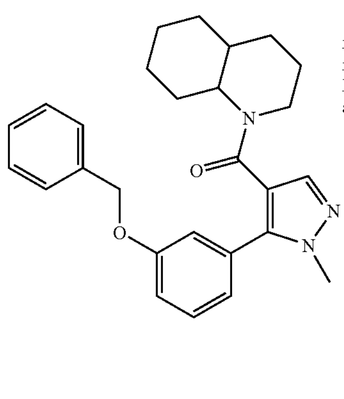 | [5-(3-Benzyloxy-phenyl)-1-methyl-1H-pyrazol-4-yl]-(octa-hydro-quinolin-1-yl)-meth-anone | A | 3-Benzyloxyphenyl-boronic acid (Aldrich Chemical Company, Inc., Milwaukee, WI) (5-Bromo-1-methyl-1H-pyrazol-4-yl)-(octa-hydro-quinolin-1-yl)-methanone (Intermediate 1) | 431 |

-continued

| Example | Structure | Name | Synthetic Method | Starting Materials | Measured Mass (M + H) |
|---|---|---|---|---|---|
| 70 | 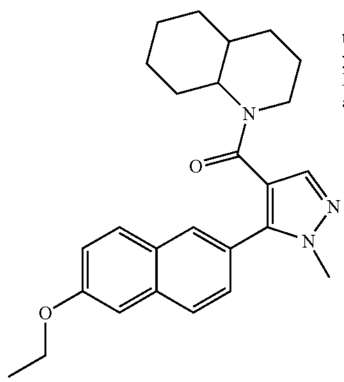 | [5-(6-Ethoxy-naphthalen-2-yl)-1-methyl-1H-pyrazol-4-yl]-(octahydro-quinolin-1-yl)-methanone | A | Ethoxy-nephthalene-2-boronic acid (Aldrich Chemical Company, Inc., Milwaukee, WI) (5-Bromo-1-methyl-1H-pyrazol-4-yl)-(octahydro-quinolin-1-yl)-methanone (Intermediate 1) | 418 |
| 71 | 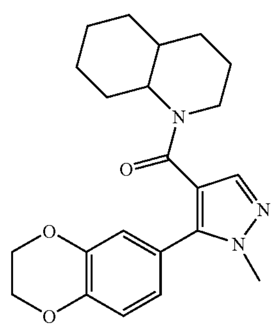 | [5-(2,3-Dihydro-benzo[1,4]dioxin-6-yl)-1-methyl-1H-pyrazol-4-yl]-(octahydro-quinolin-1-yl)-methanone | A | 2,3-Dihydro-benzo[1,4]dioxine-6-boronic acid (Frontier Scientific, Inc., Logan, UT) (5-Bromo-1-methyl-1H-pyrazol-4-yl)-(octahydro-quinolin-1-yl)-methanone (Intermediate 1) | 382 |
| 72 | 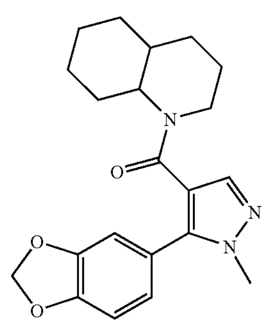 | (5-Benzo[1,3]dioxol-5-yl-1-methyl-1H-pyrazol-4-yl)-(octahydro-quinolin-1-yl)-methanone | A | Benzo[1,3]dioxole-5-boronic acid (Aldrich Chemical Company, Inc., Milwaukee, WI) (5-Bromo-1-methyl-1H-pyrazol-4-yl)-(octahydro-quinolin-1-yl)-methanone (Intermediate 1) | 368 |
| 73 | 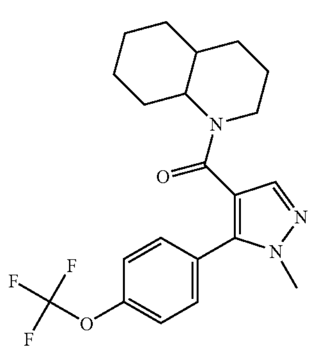 | [1-Methyl-5-(4-trifluoromethoxy-phenyl)-1H-pyrazol-4-yl]-(octahydro-quinolin-1-yl)-methanone | A | 4-Trifluoromethoxy-phenyl-boronic acid (Aldrich Chemical Company, Inc., Milwaukee, WI) (5-Bromo-1-methyl-1H-pyrazol-4-yl)-(octahydro-quinolin-1-yl)-methanone (Intermediate 1) | 408 |

-continued

| Example | Structure | Name | Synthetic Method | Starting Materials | Measured Mass (M + H) |
|---|---|---|---|---|---|
| 74 | 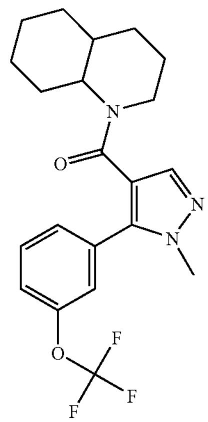 | [1-Methyl-5-(3-tri-fluoromethoxy-phe-nyl)-1H-pyra-zol-4-yl]-(octa-hydro-quinolin-1-yl)-meth-anone | A | 3-Trifluoro-methoxy-phenyl-boronic acid (Aldrich Chemical Company, Inc., Mil-waukee, WI) (5-Bromo-1-methyl-1H-pyra-zol-4-yl)-(octa-hydro-quinolin-1-yl)-meth-anone (Intermediate 1) | 408 |
| 75 | 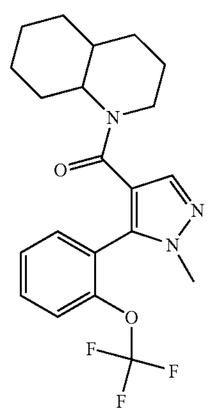 | [1-Methyl-5-(2-tri-fluoromethoxy-phe-nyl)-1H-pyra-zol-4-yl]-(octa-hydro-quinolin-1-yl)-meth-anone | A | 2-Trifluoro-methoxy-phenyl-boronic acid (Frontier Scientific, Inc., Logan, UT) (5-Bromo-1-methyl-1H-py-razol-4-yl)-(octa-hydro-quinolin-1-yl)-meth-anone (Intermediate 1) | 408 |
| 76 | 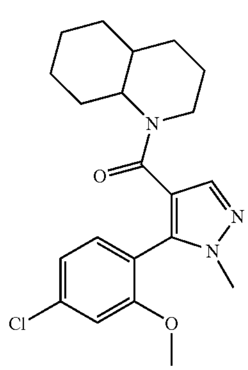 | [5-(4-Chloro-2-meth-oxy-phenyl)-1-meth-yl-1H-pyrazol-4-yl]-(octa-hydro-quinolin-1-yl)-meth-anone | A | 4-Chloro-2-meth-oxy-phenyl-boronic acid (Combi-Blocks Inc., San Diego, CA) (5-Bromo-1-methyl-1H-py-razol-4-yl)-(octa-hydro-quinolin-1-yl)-meth-anone (Intermediate 1) | 388 |

-continued

| Example | Structure | Name | Synthetic Method | Starting Materials | Measured Mass (M + H) |
|---|---|---|---|---|---|
| 77 | 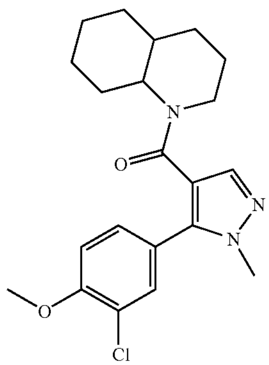 | [5-(3-Chloro-4-methoxy-phenyl)-1-methyl-1H-pyrazol-4-yl]-(octahydro-quinolin-1-yl)-methanone | A | 3-Chloro-4-methoxy-phenyl-boronic acid (Aldrich Chemical Company, Inc., Milwaukee, WI) (5-Bromo-1-methyl-1H-pyrazol-4-yl)-(octahydro-quinolin-1-yl)-methanone (Intermediate 1) | 388 |
| 78 | 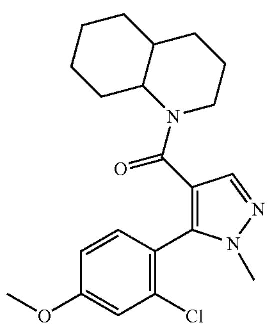 | [5-(2-Chloro-4-methoxy-phenyl)-1-methyl-1H-pyrazol-4-yl]-(octahydro-quinolin-1-yl)-methanone | A | 2-Chloro-4-methoxy-phenyl-boronic acid(Combi-Blocks Inc., San Diego, CA) (5-Bromo-1-methyl-1H-pyrazol-4-yl)-(octahydro-quinolin-1-yl)-methanone (Intermediate 1) | 388 |
| 79 | 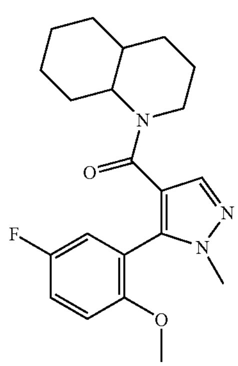 | [5-(5-Fluoro-2-methoxy-phenyl)-1-methyl-1H-pyrazol-4-yl]-(octahydro-quinolin-1-yl)-methanone | A | Fluoro-2-methoxy-phenyl-boronic acid (Aldrich Chemical Company, Inc., Milwaukee, WI) (5-Bromo-1-methyl-1H-pyrazol-4-yl)-(octahydro-quinolin-1-yl)-methanone (Intermediate 1) | 372 |
| 80 | 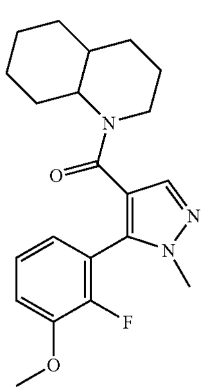 | [5-(2-Fluoro-3-methoxy-phenyl)-1-methyl-1H-pyrazol-4-yl]-(octahydro-quinolin-1-yl)-methanone | A | 2-Fluoro-3-methoxy-phenyl-boronic acid (Combi-Blocks Inc., San Diego, CA) (5-Bromo-1-methyl-1H-pyrazol-4-yl)-(octahydro-quinolin-1-yl)-methanone (Intermediate 1) | 372 |

| Example | Structure | Name | Synthetic Method | Starting Materials | Measured Mass (M + H) |
|---|---|---|---|---|---|
| 81 | 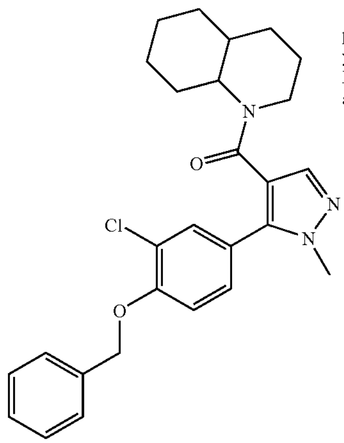 | [5-(4-Benzyloxy-3-chloro-phenyl)-1-methyl-1H-pyrazol-4-yl]-(octahydro-quinolin-1-yl)-methanone | A | 4-Benzyloxy-3-chloro-phenyl-boronic acid (Combi-Blocks Inc., San Diego, CA) (5-Bromo-1-methyl-1H-pyrazol-4-yl)-(octahydro-quinolin-1-yl)-methanone (Intermediate 1) | 464 |
| 82 | 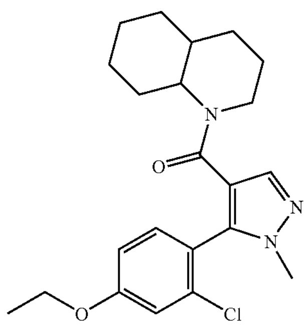 | [5-(2-Chloro-4-ethoxy-phenyl)-1-methyl-1H-pyrazol-4-yl]-(octahydro-quinolin-1-yl)-methanone | A | 2-Chloro-4-ethoxy-phenyl-boronic acid (Combi-Blocks Inc., San Diego, CA) (5-Bromo-1-methyl-1H-pyrazol-4-yl)-(octahydro-quinolin-1-yl)-methanone (Intermediate 1) | 402 |
| 83 | 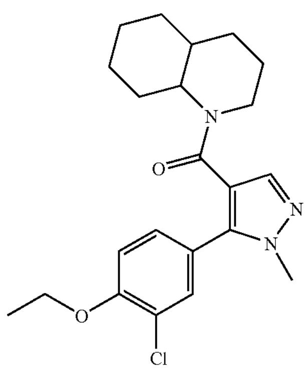 | [5-(3-Chloro-4-ethoxy-phenyl)-1-methyl-1H-pyrazol-4-yl]-(octahydro-quinolin-1-yl)-methanone | A | 3-Chloro-4-ethoxy-phenyl-boronic acid (Aldrich Chemical Company, Inc., Milwaukee, WI) (5-Bromo-1-methyl-1H-pyrazol-4-yl)-(octahydro-quinolin-1-yl)-methanone (Intermediate 1) | 402 |
| 84 | 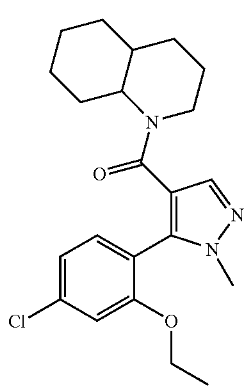 | [5-(4-Chloro-2-ethoxy-phenyl)-1-methyl-1H-pyraozl-4-yl]-(octahydro-quinolin-1-yl)-methanone | A | 4-Chloro-2-ethoxy-pheny boronic acid (Combi-Blocks Inc., San Diego, CA) (5-Bromo-1-methyl-1H-pyrazol-4-yl)-(octahydro-quinolin-1-yl)-methanone (Intermediate 1) | 402 |

-continued

| Example | Structure | Name | Synthetic Method | Starting Materials | Measured Mass (M + H) |
|---|---|---|---|---|---|
| 85 | 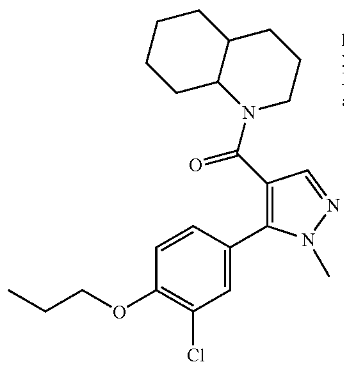 | [5-(3-Chloro-4-pro-poxy-phenyl)-1-meth-yl-1H-pyrazol-4-yl]-(octa-hydro-quinolin-1-yl)-meth-anone | A | 3-Chloro-4-propoxy-phenyl-boronic acid (Aldrich Chemical Company, Inc., Milwaukee, WI) (5-Bromo-1-methyl-1H-py-razol-4-yl)-(octa-hydro-quinolin-1-yl)-meth-anone (Intermediate 1) | 416 |
| 86 | 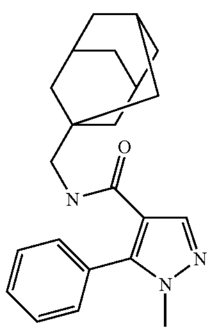 | 1-Methyl-5-phenyl-1H-py-razole-4-carboxylic acid (adamantan-1-yl-methyl)-amide | C | Methyl-5-phenyl-1H-py-razole-4-carboxylic acid (Maybridge plc, Cornwall, UK) 1-Adamantane-methyl-amine (Aldrich Chemical Company, Inc., Milwaukee, WI) | 350 |
| 87 | 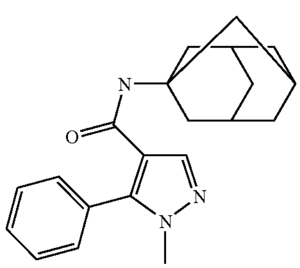 | 1-Methyl-5-phenyl-1H-py-razole-4-carboxylic acid adamantan-1-ylamide | C | Methyl-5-phenyl-1H-py-razole-4-carboxylic acid (Maybridge plc, Cornwall, UK) 1-Adamantanamine (Aldrich Chemical Company, Inc., Milwaukee, WI) | 336 |
| 88 | 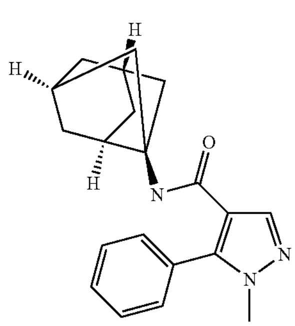 | 1-Methyl-5-phenyl-1H-py-razole-4-carboxylic acid hexahydro-2,5-meth-anopentalen-3a(1H)-amide | C | Methyl-5-phenyl-1H-py-razole-4-carboxylic acid (Maybridge plc, Cornwall, UK) 3-Aminonoradamantane hydrochloride (Aldrich Chemical Company, Inc., Milwaukee, WI) | 322 |

-continued

| Example | Structure | Name | Synthetic Method | Starting Materials | Measured Mass (M + H) |
|---------|-----------|------|------------------|--------------------|-----------------------|
| 89 | 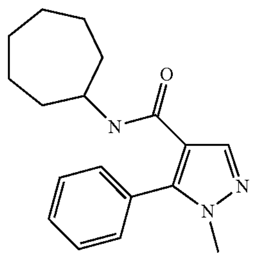 | 1-Methyl-5-phenyl-1H-pyrazole-4-carboxylic acid cycloheptylamide | C | Methyl-5-phenyl-1H-pyrazole-4-carboxylic acid (Maybridge plc, Cornwall, UK) Cycloheptylamine (Aldrich Chemical Company, Inc., Milwaukee, WI) | 298 |
| 90 | Chiral | 1-Methyl-5-phenyl-1H-pyrazole-4-carboxylic acid ((1R,2R,3R,5S)-2,6,6-trimethyl-bicyclo[3.1.1]hept-3-yl)-amide | C | Methyl-5-phenyl-1H-pyrazole-4-carboxylic acid (Maybridge plc, Cornwall, UK) (−)-Isopinocampheylamine (Aldrich Chemical Company, Inc., Milwaukee, WI) | 338 |
| 91 | Chiral | 1-Methyl-5-phenyl-1H-pyrazole-4-carboxylic acid ((1R,2S,4R)-1,7,7-trimethylbicyclo[2.2.1]hept-2-yl)-amide | C | Methyl-5-phenyl-1H-pyrazole-4-carboxylic acid (Maybridge plc, Cornwall, UK) (R)-(+)-Bornylamine (Aldrich Chemical Company, Inc., Milwaukee, WI) | 338 |
| 92 | 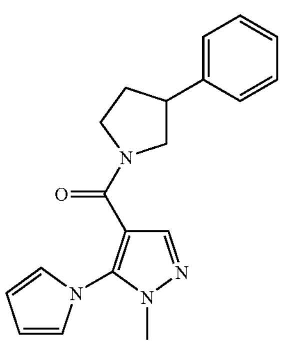 | (1-Methyl-5-pyrrol-1-yl-1H-pyrazol-4-yl-(3-phenyl-pyrrolidin-1-yl)-methanone | B | Methyl-5-pyrrol-1-yl-1H-pyrazole-4-carbonyl fluoride (Intermediate 2) 3-Phenyl-pyrrolidine (Array Biopharma Inc., Boulder, CO) | 321 |
| 93 | 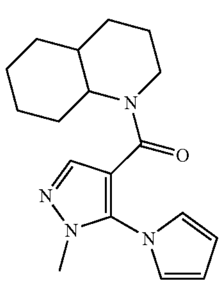 | (1-Methyl-5-pyrrol-1-yl-1H-pyrazol-4-yl-(octahydro-quinolin-1-yl)-methanone | B | Methyl-5-pyrrol-1-yl-1H-pyrazole-4-carbonyl fluoride (Intermediate 2) Decahydro-quinoline (Aldrich Chemical Company, Inc., Milwaukee, WI) | 313 |

-continued

| Example | Structure | Name | Synthetic Method | Starting Materials | Measured Mass (M + H) |
|---|---|---|---|---|---|
| 94 | (Chiral structure) | (1-Methyl-5-pyrrol-1-yl-1H-pyrazol-4-yl)-(4aR,8aS)-octahydro-isoquinolin-2-yl-methanone | B | Methyl-5-pyrrol-1-yl-1H-pyrazole-4-carbonyl fluoride (Intermediate 2) Trans-Decahydro-isoquinoline (TCI America, Portland, OR) | 313 |
| 95 | (structure) | (6-Bromo-octahydro-isoquinolin-2-yl)-(1-methyl-5-pyrrol-1-yl-1H-pyrazol-4-yl)-methanone | B | Methyl-5-pyrrol-1-yl-1H-pyrazole-4-carbonyl fluoride (Intermediate 2) 6-Bromoperhydroisoquinoline hydrobromide (available from Apollo Scientific Ltd., Cheshire, UK) | 391 |
| 96 | (structure) | 1-Methyl-5-pyrrol-1-yl-1H-pyrazole-4-carboxylic acid cyclooctylamide | B | Methyl-5-pyrrol-1-yl-1H-pyrazole-4-carbonyl fluoride (Intermediate 2) Cyclooctylamine (Aldrich Chemical Company, Inc., Milwaukee, WI) | 301 |
| 97 | (structure) | 1-Methyl-5-pyrrol-1-yl-1H-pyrazole-4-carboxylic acid adamantan-2-ylamide | B | Methyl-5-pyrrol-1-yl-1H-pyrazole-4-carbonyl fluoride (Intermediate 2) 2-Adamantanamine hydrochloride (Aldrich Chemical Company, Inc., Milwaukee, WI) | 325 |

| Example | Structure | Name | Synthetic Method | Starting Materials | Measured Mass (M + H) |
|---|---|---|---|---|---|
| 98 | 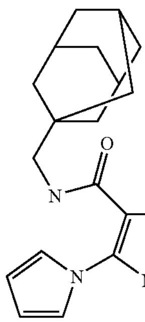 | 1-Methyl-5-pyrrol-1-yl-1H-pyrazole-4-carboxylic acid (adamantan-1-yl-methyl)-amide | B | Methyl-5-pyrrol-1-yl-1H-pyrazole-4-carbonyl fluoride (Intermediate 2) 1-Adamantane-methylamine (Aldrich Chemical Company, Inc., Milwaukee, WI) | 339 |
| 99 | 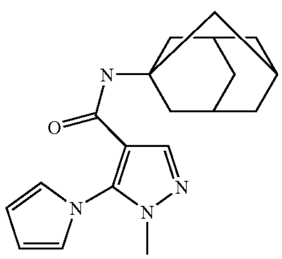 | 1-Methyl-5-pyrrol-1-yl-1H-pyrazole-4-carboxylic acid adamantan-1-ylamide | B | Methyl-5-pyrrol-1-yl-1H-pyrazole-4-carbonyl fluoride (Intermediate 2) 1-Adamantanamine (Aldrich Chemical Company, Inc., Milwaukee, WI) | 325 |
| 100 | 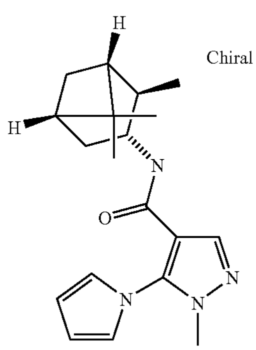 | 1-Methyl-5-pyrrol-1-yl-1H-pyrazole-4-carboxylic acid ((1R,2R,3R,5S)-2,6,6-trimethyl-bicyclo[3.1.1]hept-3-yl)-amide | B | Methyl-5-pyrrol-1-yl-1H-pyrazole-4-carbonyl fluoride (Intermediate 2) (−)-Isopinocampheylamine (Aldrich Chemical Company, Inc., Milwukee, WI) | 327 |
| 101 | 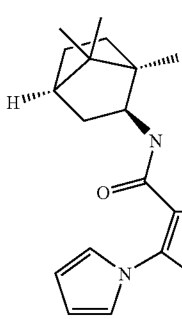 | 1-Methyl-5-pyrrol-1-yl-1H-pyrazole-4-carboxylic acid ((1R,4R)-1,7,7-trimethyl-bicyclo[2.2.1]hept-2-yl)-amide | B | Methyl-5-pyrrol-1-yl-1H-pyrazole-4-carbonyl fluoride (Intermediate 2) 1,7,7-Trimethylbicyclo[2.2.1]heptan-2-amine hydrochloride (Maybridge plc, Cornwall, UK) | 327 |

-continued

| Example | Structure | Name | Synthetic Method | Starting Materials | Measured Mass (M + H) |
|---|---|---|---|---|---|
| 102 | Chiral | 1-Methyl-5-pyrrol-1-yl-1H-pyrazole-4-carboxylic acid ((1R,2S,4R)-1,7,7-trimethylbicyclo[2.2.1]hept-2-yl)-amide | B | Methyl-5-pyrrol-1-yl-1H-pyrazole-4-carbonyl fluoride (Intermediate 2) (R)-(+)-Bornylamine (Aldrich Chemical Company, Inc., Milwaukee, WI) | 327 |
| 103 | Chiral | 1-Methyl-5-pyrrol-1-yl-1H-pyrazole-4-carboxylic acid ((1R,2R,4R)-1,7,7-trimethylbicyclo[2.2.1]hept-2-yl)-amide | B | Methyl-5-pyrrol-1-yl-1H-pyrazole-4-carbonyl fluoride (Intermediate 2) (R)-(−)-Isobornylamine hydrochloride (Fluka Chemie GmbH, Buchs, Switzerland) | 327 |
| 104 | 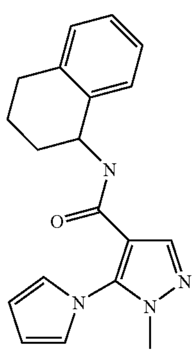 | 1-Methyl-5-pyrrol-1-yl-1H-pyrazole-4-carboxylic acid (1,2,3,4-tetrahydronaphthalen-1-yl)-amide | B | Methyl-5-pyrrol-1-yl-1H-pyrazole-4-carbonyl fluoride (Intermediate 2) 1,2,3,4-Tetrahydro-1-naphthylamine (Aldrich Chemical Company, Inc., Milwaukee, WI) | 321 |
| 105 | 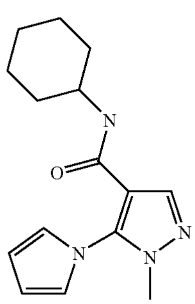 | 1-Methyl-5-pyrrol-1-yl-1H-pyrazole-4-carboxylic acid cyclohexylamide | B | Methyl-5-pyrrol-1-yl-1H-pyrazole-4-carbonyl fluoride (Intermediate 2) Cyclohexylamine (Alfa Aesar, Ward Hill, MA) | 273 |

| Example | Structure | Name | Synthetic Method | Starting Materials | Measured Mass (M + H) |
|---|---|---|---|---|---|
| 106 | 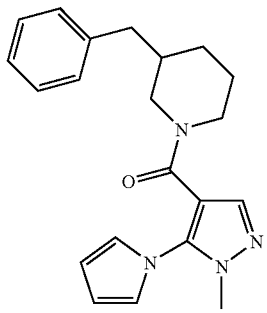 | (3-Benzyl-piperidin-1-yl)-(1-methyl-5-pyrrol-1-yl-1H-pyrazol-4-yl)-methanone | B | Methyl-5-pyrrol-1-yl-1H-pyrazole-4-carbonyl fluoride (Intermediate 2) 3-Benzyl-piperidine (Tyger Scientific Inc., Ewing, NJ) | 349 |
| 107 | 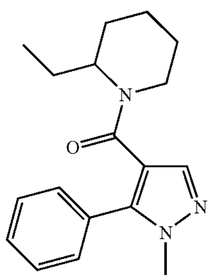 | (2-Ethyl-piperidin-1-yl)-(1-methyl-5-phenyl-1H-pyrazol-4-yl)-methanone | C | Methyl-5-phenyl-1H-pyrazole-4-carboxylic acid (Maybridge plc, Cornwall, UK) Ethyl-piperidine (Aldrich Chemical Company, Inc., Milwaukee, WI) | 298 |

Example 108

1-Methyl-5-phenyl-1H-pyrazole-4-carboxylic acid methyl-((1R,2S,4R)-1,7,7-trimethyl-bicyclo[2.2.1]hept-2-yl)-amide

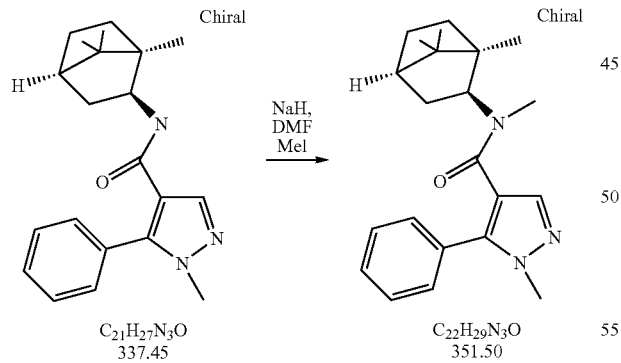

Sodium hydride (60% dispersion in mineral oil; 15 mg, 0.375 mmol) is added to a cooled (~0° C.) solution of 1-methyl-5-phenyl-1H-pyrazole-4-carboxylic acid ((1R,2S,4R)-1,7,7-trimethyl-bicyclo[2.2.1]hept-2-yl)-amide (of Example 91; 100 mg, 0.3 mmol) in dry dimethylformamide (10 mL) and the mixture is allowed to stir for 30 min. Methyl iodide (30 µL, 0.49 mmol) is added and the solution is stirred at room temperature until the reaction is complete, as judged by TLC. Water is added and the solution is extracted twice with ethyl acetate. The combined organic layers are washed with water and brine, dried (magnesium sulfate), filtered, evaporated, and purified by C-18 reversed phase HPLC with a gradient of 10-100% acetonitrile/water containing 0.1% TFA as a modifier to give 1-methyl-5-phenyl-1H-pyrazole-4-carboxylic acid methyl-((1R,2S,4R)-1,7,7-trimethyl-bicyclo[2.2.1]hept-2-yl)-amide.

Example 109

1-Methyl-5-phenyl-1H-pyrazole-4-carboxylic acid adamantan-2-yl-isopropyl-amide

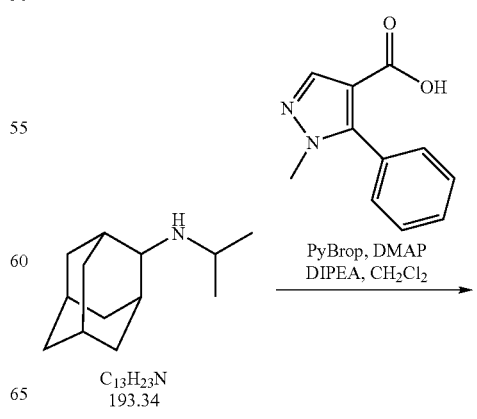

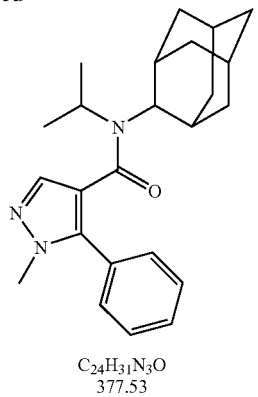

C24H31N3O
377.53

Methyl-5-phenyl-1H-pyrazole-4-carboxylic acid adamantan-2-yl-isopropyl-amide is prepared from adamantan-2-yl-isopropyl-amine (of intermediate 3) and 1-methyl-5-phenyl-1H-pyrazole-4-carboxylic acid (Maybridge plc, Cornwall, UK) according to general procedure C.

Example 110

Testing of Compounds of the Invention In Vitro

The in vitro inhibition of 11β-HSD1 by compounds of the present invention were demonstrated by means of the following test:

Purified human HSD1 was diluted in 50 mM Tris-HCl, 100 mM NaCl, 0.1 mg/ml BSA, 0.02% Lubrol, 20 mM MgCl2, 10 mM glucose 6-phosphate, 0.4 mM NADPH, 60 U/ml glucose 6-phosphate dehydrogenase to a concentration of 1.5 ug/ml (Enzyme Solution). Cortisone (100 uM) in DMSO was diluted to 1 uM with 50 mM Tris-HCl, 100 mM NaCl (Substrate Solution). Testing compounds (40 uM) in DMSO were diluted 3 fold in series in DMSO and further diluted 20 fold in Substrate Solution. Enzyme Solution (10 ul/well) was added into 384 well microtiter plates followed by diluted compound solutions (10 ul/well) and mixed well. Samples were then incubated at 37° C. for 30 min. EDTA/biotin-cortisol solution (10 ul/well) in 28 mM EDTA, 100 nM biotin-cortisol, 50 mM Tris-HCl, 100 mM NaCl was then added followed by 5 ul/well of anti-cortisol antibody (3.2 ug/ml) in 50 mM Tris-HCl, 100 mM NaCl, 0.1 mg/ml BSA and the solution was incubated at 37° C. for 30 min. Five ul per well of Eu-conjugated anti-mouse IgG (16 nM) and APC-conjugated streptavidin (160 nM) in 50 mM Tris-HCl, 100 mM NaCl, 0.1 mg/ml BSA were added and the solution was incubated at room temperature for 2 hours. Signals were quantitated by reading time-resolved fluorescence on a Victor 5 reader (Wallac).

Percent inhibition of HSD 1 activity by an agent at various concentrations was calculated by the formula % Inhibition=100*[1−(Fs−Fb)/(Ft−Fb)], where:

Fs is the fluorescence signal of the sample which included the agent,

Fb is the fluorescence signal in the absence of HSD1 and agent,

Ft is the fluorescence signal in the presence of HSD1, but no agent.

The inhibitory activities of test compounds were determined by the $IC_{50}$s, or the concentration of compound that gave 50% inhibition.

The results of the in vitro inhibition of 11β-HSD1 by representative compounds of the present invention are shown in the following Table:

| Compound | Name | IC50 (μM) |
|---|---|---|
| Example 12 | [5-(3-Isopropyl-phenyl)-1-methyl-1H-pyrazol-4-yl]-(octahydro-quinolin-1-yl)-methanone | 0.059 |
| Example 19 | (1-Methyl-5-quinolin-3-yl-1H-pyrazol-4-yl)-(octahydro-quinolin-1-yl)-methanone | 0.189 |
| Example 21 | 3-[2-Methyl-4-(octahydro-quinoline-1-carbonyl)-2H-pyrazol-3-yl]-benzaldehyde | 1.0 |
| Example 33 | [1-Methyl-5-(4-methylsulfanyl-phenyl)-1H-pyrazol-4-yl]-(octahydro-quinolin-1-yl)-methanone | 0.078 |
| Example 36 | (4-Chloro-octahydro-quinolin-1-yl)-(1-methyl-5-phenyl-1H-pyrazol-4-yl)-methanone | 0.6 |
| Example 39 | [5-(3-Chloro-4-fluoro-phenyl)-1-methyl-1H-pyrazol-4-yl]-(octahydro-quinolin-1-yl)-methanone | 0.208 |
| Example 46 | [5-(3-Chloro-2-methyl-phenyl)-1-methyl-1H-pyrazol-4-yl]-(octahydro-quinolin-1-yl)-methanone | 0.038 |
| Example 49 | [1-Methyl-5-(3-trifluoromethyl-phenyl)-1H-pyrazol-4-yl]-(octahydro-quinolin-1-yl)-methanone | 0.16 |
| Example 52 | [5-(3-Chloro-4-trifluoromethyl-phenyl)-1-methyl-1H-pyrazol-4-yl]-(octahydro-quinolin-1-yl)-methanone | 0.195 |
| Example 55 | [1-Methyl-5-(4-nitro-phenyl)-1H-pyrazol-4-yl]-(octahydro-quinolin-1-yl)-methanone | 0.552 |
| Example 59 | [5-(3-Hydroxy-phenyl)-1-methyl-1H-pyrazol-4-yl]-(octahydro-quinolin-1-yl)-methanone | 0.7 |
| Example 67 | [5-(4-Hydroxymethyl-phenyl)-1-methyl-1H-pyrazol-4-yl]-(octahydro-quinolin-1-yl)-methanone | 0.121 |
| Example 82 | [5-(2-Chloro-4-ethoxy-phenyl)-1-methyl-1H-pyrazol-4-yl]-(octahydro-quinolin-1-yl)-methanone | 0.021 |
| Example 96 | 1-Methyl-5-pyrrol-1-yl-1H-pyrazole-4-carboxylic acid cyclooctylamide | 0.058 |
| Example 106 | (3-Benzyl-piperidin-1-yl)-(1-methyl-5-pyrrol-1-yl-1H-pyrazol-4-yl)-methanone | 1.48 |
| Example 107 | (2-Ethyl-piperidin-1-yl)-(1-methyl-5-phenyl-1H-pyrazol-4-yl)-methanone | 0.26 |

Example 111

Testing of Compounds of the Invention In Vivo

The in vivo inhibition of 11β-HSD1 by compounds of the present invention can be demonstrated by means of the following test:

The compound of the invention is formulated in 7.5% Modified Gelatin in water and is administered IP at 100 mg/kg to mice (male C57Bl/6J, age ~97 Days). After 30 minutes, cortisone formulated in gelatin is administered by s.c. injection at 1 mg/kg. After a further 40 minutes, blood samples are taken from the mice and are analyzed using LC-MS for the concentrations of cortisone, cortisol, and drug.

Percent inhibition of HSD1 activity by the inhibitor is calculated by the following formula:

% Inhibition=100*[1−($C_{inh}/C_{veh}$)]

where:

$C_{veh}$ is the conversion of cortisone to cortisol when the animal is dosed with vehicle, and $C_{inh}$ is the conversion of cortisone to cortisol when the animal is dosed with inhibitor, where the conversion C is given by the formula C=[Cortisol]/([Cortisol]+[Cortisone]).

It is to be understood that the invention is not limited to the particular embodiments of the invention described above, as variations of the particular embodiments may be made and still fall within the scope of the appended claims.

What is claimed is:

1. A compound of the formula I:

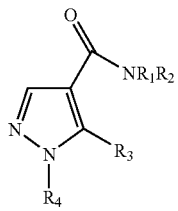

wherein:
one of $R_1$ or $R_2$ is hydrogen or alkyl and the other is lower alkyl or $(CH_2)_pY$, wherein Y is a substituted or unsubstituted, saturated, partially unsaturated, or unsaturated mono-, bi- or tri-cyclic 5-10 membered cycloalkyl ring and p is 0 or 1, and wherein substituents on Y are lower alkyl, lower alkoxy, hydroxy, hydroxy-alkyl, alkyl-phenyl, phenyl-alkyl, pyridine or halogen, wherein if one of $R_1$ or $R_2$ is lower alkyl, said lower alkyl is not substituted with cyano, or $R_1$ and $R_2$, together with the N atom to which they are attached, form a substituted or unsubstituted ring Z, wherein Z is a 5- to 7-membered monocyclic or 7- to 10-membered bicyclic saturated, partially unsaturated or unsaturated substituted or unsubstituted heterocyclic ring which contains the N atom to which $R_1$ and $R_2$ are attached, and optionally another hetero atom which is selected from N, O and S, wherein the substituted heterocyclic ring is mono- or di-substituted with lower alkyl, hydroxy, hydroxy-alkyl, alkyl-phenyl, phenyl-alkyl, pyridine or halogen;

$R_3$ is an aromatic ring system selected from the group consisting of [2,2']bithiophenyl, 1-methyl-indole, 2,3-dihydro-benzo[1,4]dioxin, benzo[1,3]dioxole, benzothiophene, dibenzofuran, furane, naphthalene, phenyl, biphenyl, quinoline, thianthrene and thiophene, wherein said aromatic ring may be unsubstituted or substituted with one or more amino, cyano, formyl, halo, hydroxy, hydroxymethyl, lower-acyl, lower-acyl-amino, lower-alkoxy, lower-alkoxy-carbonyl, 2-(lower-alkoxy-carbonyl)-ethenyl, lower-alkyl, lower-alkyl-thio, nitro, trifluoromethoxy or trifluoromethyl, wherein said phenyl ring may additionally be substituted with phenoxy or benzyloxy, or $R_3$ is:

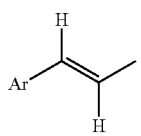

wherein Ar is a carbocyclic or heterocyclic aryl group which may be unsubstituted or substituted with one or more groups selected from the group consisting of halogen, lower alkyl, lower alkoxy, trifluoromethyl, cyano and nitro; and $R_4$ is unsubstituted lower alkyl;
and pharmaceutically acceptable salts thereof.

2. The compound according to claim 1, wherein $R_1$ is hydrogen and $R_2$ is a substituted 6-8 membered cycloalkyl ring.

3. The compound according to claim 1, wherein $R_2$ is 1,7,7-trimethyl-bicyclo[2.2.1]hept-2-yl, 2,6,6-trimethyl-bicyclo[3.1.1]hept-3-yl, 3-noradamantyl, adamantan-1-yl, adamantan-1-yl-methyl, adamantan-2-yl, 1,2,3,4-tetrahydronaphthyl, cyclohexyl, cyclooctyl, or cycoheptyl.

4. The compound according to claim 1, wherein Z is a 5-7 membered heterocyclic ring substituted with lower alkyl, hydroxy, hydroxy-alkyl, alkyl-phenyl, phenyl-alkyl, pyridine or halogen.

5. The compound according to claim 1, wherein Z is selected from the group consisting of 2-ethyl-piperidine, 3-phenyl-pyrrolidine, 3-(pyridin-3-yl)-pyrrolidine, 4-chloro-decahydro-quinolin, 4a-bromo-decahydro-isoquinoline, 6-bromo-octahydro-isoquinoline, 3-cyclohexyl-piperidine, 3-benzyl-piperidine, decahydro-quinoline and decahydro-isoquinoline.

6. The compound according to claim 1, wherein $R_3$ is substituted or unsubstituted benzothiophene or phenyl.

7. The compound according to claim 6, wherein $R_3$ is substituted with one or more halogen, lower-alkoxy or lower-alkyl.

8. The compound according to claim 1, wherein said compound is (1-Methyl-5-phenyl-1H-pyrazol-4-yl)-(trans-octahydro-isoquinolin-2-yl)methanone.

9. The compound according to claim 1, wherein said compound is [5-(4-Isopropyl-phenyl)-1-methyl-1H-pyrazol-4-yl]-(octahydro-quinolin-1-yl)-methanone.

10. The compound according to claim 1, wherein said compound is (5-Benzo[b]thiophen-2-yl-1-methyl-1H-pyrazol-4-yl)-(octahydro-quinolin-1-yl)-methanone.

11. The compound according to claim 1, wherein said compound is [5-(2-Chloro-4-methyl-phenyl)-1-methyl-1H-pyrazol-4-yl]-(octahydro-quinolin-1-yl)-methanone.

12. The compound according to claim 1, wherein said compound is [5-(2-Chloro-4-methoxy-phenyl)-1-methyl-1H-pyrazol-4-yl]-(octahydro-quinolin-1-yl)-methanone.

13. The compound according to claim 1, wherein said compound is [5-(2-Chloro-4-ethoxy-phenyl)-1-methyl-1H-pyrazol-4-yl]-(octahydro-quinolin-1-yl)-methanone.

14. The compound according to claim 1, wherein said compound is [5-(3-Chloro-4-ethoxy-phenyl)-1-methyl-1H-pyrazol-4-yl]-(octahydro-quinolin-1-yl)-methanone.

15. The compound according to claim 1, wherein said compound is 1-Methyl-5-phenyl-1H-pyrazole-4-carboxylic acid (adamantan-1-ylmethyl)-amide.

16. The compound according to claim 1, wherein said compound is 1-Methyl-5-phenyl-1H-pyrazole-4-carboxylic acid adamantan-1-ylamide.

17. The compound according to claim 1, wherein said compound is 1-Methyl-5-phenyl-1H-pyrazole-4-carboxylic acid ((1R,2R,3R,5S)-2,6,6-trimethyl-bicyclo[3.1.1]hept-3-yl)-amide.

18. The compound according to claim 1, wherein said compound is 1-Methyl-5-phenyl-1H-pyrazole-4-carboxylic acid ((1R,2S,4R)-1,7,7-trimethyl-bicyclo[2.2.1]hept-2-yl)-amide.

19. A pharmaceutical composition comprising a therapeutically effective amount of a compound according to formula (I):

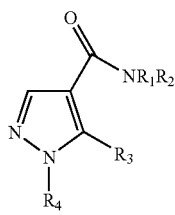

(I)

wherein:
- one of $R_1$ or $R_2$ is hydrogen or alkyl and the other is lower alkyl or $(CH_2)_p Y$, wherein Y is a substituted or unsubstituted, saturated, partially unsaturated, or unsaturated mono-, bi- or tri-cyclic 5-10 membered cycloalkyl ring and p is 0 or 1, and wherein substituents on Y are lower alkyl, lower alkoxy, hydroxy, hydroxy-alkyl, alkyl-phenyl, phenyl-alkyl, pyridine or halogen, wherein if one of $R_1$ or $R_2$ is lower alkyL said lower alkyl is not substituted with cyano,
- or $R_1$ and $R_2$, together with the N atom to which they are attached, form a substituted or unsubstituted ring Z, wherein Z is a 5- to 7-membered monocyclic or 7- to 10-membered bicyclic saturated, partially unsaturated or unsaturated substituted or unsubstituted heterocyclic ring which contains the N atom to which $R_1$ and $R_2$ are attached, and optionally another hetero atom which is selected from N, O and S, wherein the substituted heterocyclic ring is mono- or di-substituted with lower alkyl, hydroxy, hydroxy-alkyl, alkyl-phenyl, phenyl-alkyl, pyridine or halogen;

$R_3$ is an aromatic ring system selected from the group consisting of [2,2']bithiophenyl, 1-methyl-indole, 2,3-dihydro-benzo[1,4]dioxin, benzo[1,3]dioxole, benzothiophene, dibenzofuran, furane, naphthalene, phenyl, biphenyl, quinoline, thianthrene and thiophene, wherein said aromatic ring may be unsubstituted or substituted with one or more amino, cyano, formyl, halo, hydroxy, hydroxymethyl, lower-acyl, lower-acylamino, lower-alkoxy, lower-alkoxy-carbonyl, 2-(lower-alkoxy-carbonyl)-ethenyl, lower-alkyl, lower-alkyl-thio, nitro, trifluoromethoxy or trifluoromethyl, wherein said phenyl ring may additionally be substituted with phenoxy or benzyloxy, or $R_3$ is:

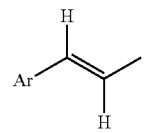

wherein Ar is a carbocyclic or heterocyclic aryl group which may be unsubstituted or substituted with one or more groups selected from the group consisting of halogen, lower alkyl, lower alkoxy, trifluoromethyl, cyano and nitro; and $R_4$ is unsubstituted lower alkyl;

or pharmaceutically acceptable salts thereof,
and a pharmaceutically acceptable carrier.

* * * * *